US009560697B2

(12) United States Patent
Junghans et al.

(10) Patent No.: US 9,560,697 B2
(45) Date of Patent: Jan. 31, 2017

(54) FLEXIBLE HEATED PLANAR ELEMENT

(75) Inventors: Monika Junghans, Hamburg (DE);
Bernd Dietz, Ammersbek (DE); Frank Domann, Uetersen (DE); Udo Dominikat, Wees (DE); Klaus Keite-Telgenbüscher, Hamburg (DE); Ute Ellringmann, Hamburg (DE)

(73) Assignee: TESA SE, Norderstedt (DE)

( * ) Notice: Subject to any disclaimer, the term of this patent is extended or adjusted under 35 U.S.C. 154(b) by 634 days.

(21) Appl. No.: 12/507,466

(22) Filed: Jul. 22, 2009

(65) Prior Publication Data

US 2010/0021683 A1    Jan. 28, 2010

(30) Foreign Application Priority Data

Jul. 24, 2008   (DE) .................. 10 2008 034 748

(51) Int. Cl.
*B32B 3/22* (2006.01)
*B32B 3/24* (2006.01)
(Continued)

(52) U.S. Cl.
CPC ............ *H05B 3/34* (2013.01); *H05B 3/845* (2013.01); *A61K 9/0009* (2013.01); *A61K 9/703* (2013.01); *B32B 3/22* (2013.01); *B32B 3/266* (2013.01); *B32B 7/12* (2013.01); *B32B 15/08* (2013.01); *B32B 15/16* (2013.01); *B32B 2250/03* (2013.01);
(Continued)

(58) Field of Classification Search
CPC ...................................................... H01H 1/029
See application file for complete search history.

(56) References Cited

U.S. PATENT DOCUMENTS 3,438,843 A * 4/1969 Pagel .................. C09J 7/00
                                                        156/179
3,757,087 A * 9/1973 Bernard ................ H01R 4/02
                                                        174/117 A
(Continued)

FOREIGN PATENT DOCUMENTS

DE         29 48 350        6/1980
DE           272753     * 10/1989   ............... H05B 3/12
(Continued)

OTHER PUBLICATIONS

English Abstract for JP 03020378 A, Jan. 1991.*
(Continued)

*Primary Examiner* — Jeff Vonch
(74) *Attorney, Agent, or Firm* — Norris McLaughlin & Marcus, P.A.

(57) ABSTRACT

A double-sidedly self-adhesive planar element which is intrinsically heatable in a self-regulating way and at the same time has a particularly high flexibility. The planar element has a layer sequence of a posistor heating layer, a contacting layer and an adhesive layer, the contacting layer being a two-dimensional perforate contacting element which within the planar element is therefore present as a contacting element which has not been applied to a backing. Also disclosed is an adhesively bonded assembly of a bonding substrate and a planar element of the aforesaid kind, a method of producing a planar element of the aforesaid kind, and a method of using a planar element of the aforesaid kind for heating an adhesively bonded assembly.

23 Claims, 6 Drawing Sheets

(51) Int. Cl.
*B32B 7/10* (2006.01)
*B32B 15/02* (2006.01)
*B32B 15/04* (2006.01)
*H05B 3/34* (2006.01)
*H05B 3/36* (2006.01)
*H05B 3/38* (2006.01)
*H01C 7/02* (2006.01)
*C09J 9/02* (2006.01)
*C09J 7/00* (2006.01)
*A61K 9/70* (2006.01)
*A61K 50/00* (2006.01)
*H05B 3/84* (2006.01)
*B32B 7/12* (2006.01)
*B32B 15/08* (2006.01)
*B32B 3/26* (2006.01)
*B32B 15/16* (2006.01)
*A61K 9/00* (2006.01)

(52) U.S. Cl.
CPC ...... *B32B 2250/04* (2013.01); *B32B 2264/108* (2013.01); *B32B 2307/30* (2013.01); *B32B 2307/704* (2013.01); *C09J 7/00* (2013.01); *C09J 9/02* (2013.01); *C09J 2203/30* (2013.01); *H01C 7/021* (2013.01); *H01C 7/027* (2013.01); *H05B 3/36* (2013.01); *H05B 3/38* (2013.01); *H05B 2203/006* (2013.01); *H05B 2203/013* (2013.01); *H05B 2203/017* (2013.01); *H05B 2203/02* (2013.01); *H05B 2214/04* (2013.01); *Y10T 156/10* (2015.01); *Y10T 428/24149* (2015.01); *Y10T 428/24314* (2015.01); *Y10T 428/24331* (2015.01); *Y10T 428/24851* (2015.01); *Y10T 428/24917* (2015.01); *Y10T 428/26* (2015.01); *Y10T 428/265* (2015.01); *Y10T 428/28* (2015.01); *Y10T 428/2804* (2015.01); *Y10T 428/2848* (2015.01); *Y10T 428/2852* (2015.01)

(56) References Cited

U.S. PATENT DOCUMENTS

| | | | | |
|---|---|---|---|---|
| 3,996,402 A | * | 12/1976 | Sindt | B29C 65/4815 156/272.4 |
| 3,999,040 A | * | 12/1976 | Ellis | 219/543 |
| 4,028,276 A | * | 6/1977 | Harden | H01C 7/027 252/511 |
| 4,775,778 A | | 10/1988 | Van Konynenburg et al. | |
| 4,860,434 A | * | 8/1989 | Louison | D06F 75/24 156/218 |
| 4,910,380 A | * | 3/1990 | Reiss | B32B 17/10036 15/250.05 |
| 5,038,796 A | * | 8/1991 | Axelgaard | A61N 1/0452 607/152 |
| 5,198,639 A | * | 3/1993 | Smuckler | B60R 1/0602 219/219 |
| 2007/0007267 A1 | * | 1/2007 | Rayl et al. | 219/217 |
| 2007/0007269 A1 | * | 1/2007 | Kim | C22C 1/002 219/260 |
| 2007/0029309 A1 | * | 2/2007 | Keite-Telgenbuscher et al. | 219/549 |
| 2008/0083740 A1 | * | 4/2008 | Kaiserman et al. | 219/520 |

FOREIGN PATENT DOCUMENTS

| | | | |
|---|---|---|---|
| DE | 103 10 722 | | 9/2004 |
| DE | 10 2007 007617 | | 8/2008 |
| EP | 256756 A2 | * | 2/1988 |
| EP | 0 307 205 | | 3/1989 |
| EP | 03 11 142 | | 4/1989 |
| EP | 0 435 923 | | 7/1991 |
| EP | 0 512 703 | | 11/1992 |
| EP | 0 852 801 | | 7/1998 |
| EP | 04 712 016 | | 9/2004 |
| JP | 60028195 A | * | 2/1985 |
| JP | 03020378 A | * | 1/1991 ............... C09J 9/02 |
| JP | 03131679 A | * | 6/1991 |
| JP | 09048952 A | * | 2/1997 |
| JP | 2002110322 A | * | 4/2002 |
| WO | 2004 081136 | | 9/2004 |

OTHER PUBLICATIONS

English Abstract for JP 03131679 A, Jun. 1991.*
Donatas Satas "Handbook of Pressure Sensitive Technology" Van Nostrand, New York 1989.
Skelhorne "Electron Beam Processing" Chemistry and Technology of UV and EB formulations for Coatings, Inks and Paints, vol. 1, 1991, SITA, London.

* cited by examiner

FLEXIBLE HEATED PLANAR ELEMENT

The invention relates to a planar element having a first self-adhesive side face and a second self-adhesive side face, the planar element featuring a layer sequence comprising a heating layer, a contacting layer and an adhesive layer, wherein the heating layer is in contact, and in electrically conducting communication, with a first side face of the contacting layer, and wherein the adhesive layer is in contact with a second side face of the contacting layer, and where the heating layer is composed of an intrinsically heatable first self-adhesive designed as a posistor which heats up when an electric current is passed through, and wherein the adhesive layer is composed of a second self-adhesive. The invention further relates to an adhesively bonded assembly comprising a planar element of this kind and a bonding substrate; a method of producing the planar element; and the use of this planar element for bonding substrates in the automotive industry and also for heating an adhesively bonded assembly.

There are many areas where electrical heating is used to heat articles or spaces. In electrical heating, heat in the form of thermal energy is obtained by conversion from electrical energy (including magnetic energy). Electrical heating may fundamentally be based on different technical principles.

Besides the generation of heat on the basis of capacitive or inductive effects or of electromagnetic radiation, heating systems have become established that include a resistance heating element (and are known as resistance heaters). In systems of this kind the thermal energy that comes about when an electrical current is passed through the resistance heating element (Joule heat) is utilized. In principle, as the resistance heating element, it is possible here to use any electrical conductor that has a non-zero finite resistance value.

The selection of the resistance heating element is made on the basis of the heat performance to be obtained, which is dependent in turn on the resistance value of the resistance heating element and on the electrical current flowing through the resistance heating element, and therefore, in accordance with Ohm's law, on the applied voltage. Consequently the resistance heating element is selected in accordance with the nature of the conduction pathways it contains, more particularly in accordance with its cross-section, length, specific resistance, and thermal load-bearing capacity.

In the automotive industry in particular the use of resistance heaters is on the increase—for the purpose, for instance, of heating car seats, car windows and external mirrors. In order to bring about the desired heating in such applications, the simplest systems involve resistance wires that are laid flatly. In that case the heating output is constant and is regulated via an external mechanism.

In recent years, elements known as PTC elements have become established as resistance heating elements in these applications. A PTC element is a resistance heating element whose current-conducting regions are composed of a material which has a positive temperature coefficient (PTC); these materials are also referred to as posistors.

Posistors are therefore materials which conduct electrical current and whose resistance increases with temperature, and they therefore conduct current more effectively at lower temperatures than at high temperatures. The use of materials of this kind with posistor behaviour as resistance heating elements (PTC elements) affords the advantage that, when a constant voltage is applied to such a heating element, the overheating of the element is prevented, since, in the case of an increase in the operating temperature, there is an increase in the resistance of the heating element, as a result of which, in accordance with Ohm's law, the current reduces in proportion to the increase in resistance, the overall heat output decreases, and the heating element cools down again. Depending on the specific application, an intrinsic regulation of this kind can be used to limit temperature instead of or in addition to an external regulating system.

In automotive engineering as well it has become established to use PTC elements of this kind. For instance, for external vehicle mirrors, PTC elements contacted with aluminium conductor faces, for example, are bonded, and connect the reverse of the mirror glass to a backing plate in the mount of the mirror. When a voltage is then applied to the PTC element, it heats up as a result of the current flow. The heat that this generates is transmitted via a double-sided pressure-sensitive adhesive tape to the glass surface of the mirror, thereby heating it. In this way it is possible to obtain temperatures of 45° C. to 80° C. on the glass surface of the mirror.

The posistors used in this kind of adhesively bondable heating element are generally partially crystalline thermoplastics, such as polyethylene, polyvinylidene fluoride, hexafluoropropylene or tetrafluoroethylene, for instance, that contain carbon black. The state of the art is described in detail in DE 29 48 350 A1, EP 0 307 205 A1, EP 0 512 703 A1 and EP 0 852 801 A1. In their mirror heating utility, these posistors are applied in the form of an ink to a continuous conductor face which serves as an electrical contacting electrode disposed on a separate backing foil with a thickness of typically 75 µm to 250 µm. The solvent contained in the ink is removed in a concluding step of drying. Such inks are described comprehensively in EP 0 435 923 A1.

The existing system of backing foil with conductor faces and intrinsically heatable coating material is sufficient to obtain heating but necessitates a relatively complicated construction, since the individual components of the heating element must be bonded not only to the glass of the mirror but also to the backing plate of the mirror, which in many cases is composed of the plastic acrylonitrile/butadiene/styrene (ABS). The adhesive bonding of these different materials imposes particular requirements on the adhesive tape.

In addition to the considerations based on the materials of the particular substrate, it is necessary with a pressure-sensitive adhesive tape of this kind, which is used to fix the heating element to the mirror plate and which transports the heat from the heating element to the mirror surface, for there to be not only a very high thermal conductivity but also particular adaptations in respect of the thermal shear strength at elevated temperatures and also the weathering resistance and pressure-sensitive adhesion at low temperatures. This applies likewise to a separate adhesive layer that is provided for fixing the composite tape, comprising backing foil and conductive ink, to the backing plate of the mirror mounting.

Further requirements imposed on the composite tape comprising adhesive tape, backing foil with conductor faces, and intrinsically heatable coating material relate to the anti-splintering functionality of this composite tape, the composite tape being intended to prevent effectively release of splinters in the event of breakage of the mirror. This is generally achieved with the use of a further backing foil in the adhesive tape.

All in all, however, the flexibility of a composite tape of this kind is low at best. Consequently the heating elements that are known from the prior art and can be bonded in the form of a composite tape possess the disadvantage that they are relatively rigid. The composite tape therefore adheres poorly to a curved substrate, since the strength of the composite tape opposes deformation with a high mechanical resistance. As a result of this there may be local or complete detachment of the heating element from the bonding substrate (support), which reduces or even prevents the transmission of the electrically generated thermal energy to the bonding substrate. Moreover, the rigidity of the construction of conventional bondable heating elements is detrimental to the mechanical low-temperature impact strength of a bond between different bonding substrates, such as between a mirror and a mirror mount.

In the case of large and curved substrate surfaces in particular, a problem which arises is that differing gap dimensions occur over the surface as a result of manufacturing tolerances (such as of mirror glass and support plate), and often prevent a full-area adhesive bond. These regions may, furthermore, be penetrated by liquid or gaseous media (fluids), such as rainwater or condensation, for example, which may further reduce the strength of the adhesive bond.

This effect is problematic in particular in the case of rearview car mirrors which have a single-piece mirror with an extended range of view, wherein the mirror has a surface curved in two spatial directions (wide-angle mirrors or close-proximity mirrors). In the case of such a curvature in two dimensions, bonding of the mirror to the bondable heating element is prevented by the rigid backing foil on which the conductor face structures are applied. In addition to the backing foil, the conductor faces as well are a hindrance to bonding to a curved substrate, since they are composed of comparatively rigid metal layers, conductive coating materials or printing inks, which may break if stretched or bent significantly, meaning that the electrical contact in these systems is not reliably ensured.

A further problem, arising in the case of modern exterior car mirror constructions, is that, in addition to the bondable heating element, there are further functionalities to be realized in the external car mirror (such as electrochromic dimming of the mirror, for instance), whose realization likewise contributes to the installed depth or overall thickness of the component. As a consequence of such increasingly thick functional and bonding constructions, their increasing thickness a consequence of the functional structures required, between the mirror glass itself and the support plate, the freedom of the designer in the design of the car mirror is significantly restricted and, moreover, the weight of the external mirror as a whole is increased.

An improvement has been achieved through joint realization of the electrically conducting structures of the heating element with the adhesive tape in one planar element. A pressure-sensitively adhesive planar element of this kind which is intrinsically heatable and combines the heating function with the pressure-sensitive adhesion is described in DE 103 10 722 A1. As a disadvantage of this construction, however, it has emerged that the adhesive increasingly loses pressure-sensitive adhesion in line with its fraction as a proportion of electrically conducting constituents by means of which, therefore, the heating of the adhesive is possible to start with. In this case, furthermore, it is sometimes difficult to form a sufficiently pronounced posistor behaviour at all with the generally amorphous pressure-sensitively adhesive polymers.

With this construction as well, in addition, there is still the problem of inadequate flexibility of the planar element, consequently lowering considerably the reliability of an adhesive bond, which in turn results in reduced mechanical, electrical and thermal contact via the bond, so decreasing the maximum quantity of heat that can be utilized, and making heat transfer more difficult.

It is an object of the present invention, therefore, to provide a planar element that eliminates these disadvantages and is formed in such a way that it allows effective mechanical and electrical contact even to a substrate with a curved surface, while at the same time exhibiting a high bond strength on that substrate and, furthermore, having a simple construction, allowing it to be produced favourably from the standpoints of economics and environment. A particular object was to provide an improved intrinsically heatable and double-sidedly bonding planar element that offers increased flexibility and/or enhanced gap bridging and also a thinner construction.

This object is achieved, surprisingly and unforeseeably for the skilled person, by a planar element of the type specified at the outset, in which the contacting layer is an at least substantially two-dimensionally extended perforate contacting element. The two-dimensionally perforate form of the contacting element gives it a flexible quality and therefore an increased fracture resistance. The contacting element in this case gains in flexibility parallel to the principal extent (plane of principal extension) of the planar element, and so the contacting element, in response to a force acting transverse to the principal extent, is movably flexible, without breaking under the resulting mechanical stress. At the same time, the at least substantially two-dimensional extent of the contacting element ensures that the cross-section of the contact face with the heating layer, that conducts the electrical current, is sufficiently large to ensure extensive heating and so to safeguard the principal functionality.

The planar element of the invention therefore does not require a stabilizing backing foil that lowers its flexibility. In this context it is found, surprisingly, that the planar element of the invention exhibits a higher bond strength than corresponding prior-art constructions. Thus, as a result of the particularly flexible formation, the anti-splintering criterion is met even without an additional backing foil. Furthermore, in the use of a planar element of this kind, a bond can be obtained that has a thickness of a kind otherwise achieved only by using unheated double-sided adhesive tapes, so making it possible to work against a thick overall construction.

It is favourable, moreover, if, in addition to the features of the aforementioned formation, the planar element is formed in such a way that all of the sub-regions of the perforate contacting element are in electrically conducting connection with one another through the perforate contacting element. In this way the contacting element is formed as a single electrode (pole) of the heating layer, and so the current is able to pass through the entire area of contact (contact face) of the contacting element with the posistor heating layer and so is able to effect virtually full-area heating of the planar element. In this way it is possible to provide a high heating output extensively over a maximum area. The second contacting of the heating layer (the other electrode or the other pole) is then performed via a further contacting element which is provided outside of the planar element: for example, a metallic layer which is a good current conductor on one substrate, or else a metal layer on the other substrate.

Instead of the aforementioned design, however, it may also be of advantage if the perforate contacting element has at least two sub-regions which are not in electrically conducting connection with one another via the perforate contacting element. Via separate sub-regions of this kind, which may be formed, for example, as a multiplicity of individual sub-sections, it is possible to realize both electrical contacts (electrodes or poles) that are necessary for a heating action on the part of the heating layer within the contacting element, thereby making it possible to dispense with further current-conducting layers outside the planar element, and hence greatly simplifying the final assembly of the planar element on the bonding substrates. Furthermore, it is also possible to apply different voltages to each of the individual sub-sections of the planar element, in order, for instance, to generate a voltage gradient in the area of the planar element and to adapt the heating output individually to the particular requirements.

In addition to the features of one or more of the aforementioned forms it is favourable, moreover, if the perforate contacting element has perforations whose principal extent runs at least substantially in one spatial direction, the preferential direction. In this way it is possible to obtain a particularly high level of flexibility of the planar element in one direction in conjunction with minimal adverse effects on the mechanical stability and on the electrical contact cross-section. This may be especially sensible, for instance, when the planar element is to be fixed to a surface like that of the outside of a cylinder, which is highly curved in one direction and has a small radius of curvature.

It may further be of advantage for the perforate contacting element to have a branched comb structure or finger structure. A form of this kind allows optimum utilization of virtually the whole area of the planar element for heat generation with only small perforations, without significantly adversely affecting the mechanical properties or raising the likelihood of a sharp drop in voltage over the layer. In the case of a comb structure and in the case of a finger structure (interdigital structure), individual teeth or fingers branch off from a main strand. The main strand in this case may have a larger cross-section than the teeth or fingers, or else may have the same cross-section. The difference between a comb structure and a finger structure is that in the case of a comb structure the elements that branch off are disposed on the same side of the main strand, whereas in the case of a finger structure they branch off from different sides. Both structures may have either single or multiple branches and both regular and irregular arrangements, and can be employed when the contacting element is designed as a single electrode or when the contacting element is designed as a plurality of electrodes within the contacting layer.

With regard to the first self-adhesive it is favourable for it to comprise, in addition to the features of one or more of the aforementioned embodiments, at least one electrically conductive filler. In this way it is possible with particular ease and cost-effectiveness to obtain a posistor adhesive which offers a heating output that is sufficiently high for numerous applications. It is particularly advantageous in this context if the electrically conducting filler is selected from the group encompassing graphite, carbon nanoparticles and carbon black, more particularly conductive carbon black. The advantage of such a composition is that these fillers exhibit particularly good connection to the polymer matrix, with the consequence that an adhesive of this kind possesses high cohesion overall and therefore has strong mechanical load-bearing capacity.

With regard to the posistor properties of the first self-adhesive, it is particularly favourable in this case if the first self-adhesive features partially crystalline polymers or even partially crystalline block copolymers, more particularly in a fraction of more than 30% by weight in the first self-adhesive, preferably of more than 50% by weight. This offers the advantage that, in this way, it is possible as the first self-adhesive to employ adhesives which as well as good technical properties exhibit a high conductivity and at the same time a strongly pronounced posistor behaviour, allowing them to limit the current to a particular degree and therefore to counteract overheating efficiently.

With these embodiments, furthermore, it has proven to be favourable if the electrically conducting filler is present in the first self-adhesive in a fraction of 1% to 60% by weight, preferably in a fraction of 5% to 30% by weight, since in that way it is possible to realize adhesives which on the one hand have a sufficiently high conductivity (allowing a current to flow through the self-adhesive at all) and at the same time have a sufficiently low conductivity (so that the heat produced on the basis of the drop in voltage at the resistor is not too great), thereby making them suitable overall as posistor heating compositions, but also which possess a high adhesive fraction, thereby ensuring, moreover, the bond strength.

In addition to the features of one or more of the aforementioned embodiments it has emerged as being favourable for the first self-adhesive and/or the second self-adhesive to be a pressure-sensitive adhesive. Systems of this kind allow particularly simple bonding, without the need for further operating steps such as heating of the planar elements, for instance, and so self-adhesives of this kind can be employed even with a substrate which has a highly irregular geometry or is heat-sensitive.

Pressure-sensitive adhesives (PSAs) which have emerged as being advantageous are in particular those which are based at least partly on at least one acrylic monomer of the general formula $CH_2=C(R^1)(COOR^2)$, $R^1$ being selected from the group encompassing H and $CH_3$ and $R^2$ being selected from the group encompassing H and also saturated or unsaturated, unbranched or branched, substituted or unsubstituted $C_1$ to $C_{30}$ alkyl radicals, particularly such that the PSA is based at least partly on at least one acrylic monomer of the general formula $CH_2=C(R^1)(COOR^{2\prime})$ where $R^1$ is selected from the group encompassing H and $CH_3$ and $R^{2\prime}$ is selected from the group encompassing H and saturated, unbranched or branched, substituted or unsubstituted $C_2$ to $C_{20}$ alkyl radicals, and also, furthermore, is based at least partly on a comonomer which is polymerizable with said at least one acrylic monomer and which is selected in particular from the group encompassing vinyl compounds with functional groups, maleic anhydride, styrene, styrene compounds, vinyl acetate, acrylamides or photoinitiators that are functionalized with double bonds. Instead, however, the PSA may also comprise at least partly a natural rubber compound and/or a synthetic rubber compound, and also silicone adhesive. PSAs of this kind offer the advantage that the technical properties of the planar element can be controlled in a broad scope and can therefore be tailored to the specific conditions of the bond to be achieved, in respect of the particular substrate or the ambient conditions, for instance.

Instead of being embodied as a pressure-sensitive adhesive, it may be advantageous, in addition to the features of one or more of the aforementioned embodiments, if the first self-adhesive and/or the second self-adhesive is a hotmelt adhesive. By means of a hotmelt adhesive of this kind it is possible to obtain a particularly high bond strength, which is why such systems are employed especially where the adhesive bond is subject to severe mechanical loads. An embodiment of this kind does not of course rule out one of the two self-adhesives (first self-adhesive and second self-adhesive) being a PSA and the other of the two self-adhesives being a hotmelt adhesive.

Hotmelt adhesives which have emerged as being advantageous are especially those which are selected from the group encompassing polyolefins and copolymers of polyolefins, and also their acid-modified derivatives, ionomers, polyamides and their copolymers, and block copolymers such as styrene block copolymers. By means of these adhesive systems it is possible to control the technical properties of the planar element in a particularly broad scope in conjunction with the high bond strength and therefore to tailor them to the specific circumstances of the bond to be obtained.

In addition to the features of one or more of the aforementioned embodiments it has emerged as being favourable if the composition of the first self-adhesive is identical to the composition of the second self-adhesive. In this way it is possible to realize an intrinsically heatable planar element with particularly high heating output in an extremely simple way. Instead, however, it may also be sensible for the composition of the first self-adhesive to be different from the composition of the second self-adhesive, so making it possible, in particular, to bond two bonding substrates of different types to one another, such as a polar glass surface to an apolar polymer surface, a polyolefin, for instance.

In addition to the features of one or more of the aforementioned embodiments it has emerged as being favourable if the planar element has a third self-adhesive on the side face of the heating layer that faces away from the perforate contacting element. By this means it is possible to decouple the technical properties of the first self-adhesive from those of the self-adhesive side faces of the planar element. Accordingly, it is possible to achieve a particularly high bond stability overall, since the adhesives can be tailored individually to the particular substrate on the self-adhesive side faces of the planar element, and at the same time the heating layer can be adapted for particularly good anchoring on the contacting element, which is especially important when the material of the surface of the contacting element is very different from the material of the surface of the substrate, such as in the case of a metallic contacting element and a polyolefinic substrate, for instance.

In addition to the features of one or more of the aforementioned embodiments, the planar element may have a heating layer thickness of less than 1 mm, preferably a thickness from a range from 10 µm to 400 µm, more preferably from a range from 20 µm to 200 µm. Embodying the heating layer in this way ensures optimum properties, since on the one hand the heating layer is thick enough to provide a sufficiently high heating output while on the other hand it is thin enough to ensure rapid thermal conduction within the heating layer and also good mechanical properties in respect of flexibility and cohesion.

It is of advantage, furthermore, if the planar element, in addition to the features of one or more of the aforementioned embodiments, comprises a flexible permanent backing. This produces a particularly stable planar element with a high degree of flexibility. Instead of this, however, the planar element may also be of backing-free form. This is especially favourable when a particularly high flexibility is required and/or a low installed depth of the planar element is required.

With regard to ease of handling, moreover, it has emerged as being sensible for the planar element, in addition to the features of one or more of the aforementioned embodiments, to have a temporary backing on its first self-adhesive side face and/or on its second self-adhesive side face. As a result of such a backing it is possible to prevent unintended sticking in the course of production, storage and bonding and so to make these steps easier.

In accordance with a further aspect of the present invention an adhesively bonded assembly is proposed comprising a bonding substrate and one of the aforementioned planar elements. The adhesively bonded assemblies known to date have the disadvantage that they cannot be reliably bonded durably to curved (bent) surfaces, since the inherent rigidity of the self-adhesive planar elements bonded to them on one side may result in detachment from the curved surface. This disadvantage is avoided by using the planar element of the invention. The element is favourable in particular when the adhesively bonded assembly is an assembly of at least one double-sidedly self-adhesive planar element and a viewing plate or mirror plate as bonding substrate, since the high intrinsic weight of the bonding substrate in systems of this kind means that detachment of the bonding substrate from the mount and the destruction of the bonding substrate that is a potential result of this are particularly problematic.

Furthermore, the present invention proposes the use of the above-described planar element for bonding substrates in the automotive industry, more particularly for heating the aforementioned adhesively bonded assembly. Where an adhesively bonded assembly of the type known to date, bonded to a bonding substrate with a curved surface, is intrinsically heated, the heating of the adhesive is accompanied by its softening and hence also by a decrease in its cohesion. Owing to the high inherent rigidity of the planar elements used to date, this may result in splitting of the softened adhesive, and the detachment of the adhesively bonded assembly from the bonding substrate. This disadvantage is avoided by using the planar element of the invention to heat the adhesively bonded assembly.

Also possible in accordance with the invention, furthermore, is a use wherein a planar element of this kind is bonded on the surface of a human or animal body, for the purpose, for example, of releasing an encapsulated active substance to the skin or to the top side of the pelt, in the form, for instance, of a topically active or transdermal patch. In this case the planar element has at least one active substance which can be released by heat or whose release is supported by heat. In this way, with particular simplicity, it is possible for there to be time-controlled and quantitatively controlled release of the corresponding active substances.

Finally the present invention provides a method of producing a planar element that comprises the steps of forming a first adhesive stratum, applying the perforate contacting element directly to the surface of the first adhesive stratum, and applying a second adhesive stratum to the surface of the perforate contacting element. With the methods to date the contacting element has always been used on a permanent backing, thus giving only thick planar elements with generally low flexibility. As a result of the application of the contacting element directly to the surface of an adhesive, it is possible, with a low level of operational complexity, to obtain planar elements of low thickness without having for that purpose to apply the contacting element separately to a backing (permanent or temporary), thus resulting overall in a simplification of the production method.

Unless indicated otherwise, the individual advantageous embodiments can be combined with one another as desired and used to obtain the advantageous effects described above and also others; these features are therefore also considered protectable per se in combination with the features of the independent claims.

Given below, for the purpose of illustrating the invention, is a general description of the invention, including a description of certain representative examples of individual constituents of part-aspects of the invention, which may be linked with one another almost arbitrarily as a function of the particular properties desired.

In principle the invention provides a planar element having a first self-adhesive side face and a second self-adhesive side face. Planar elements for the purpose of this specification include in particular all customary and suitable structures having a substantially two-dimensional extent. They enable bonding and may be of various embodiments, more particularly flexible, in the form of an adhesive sheet, adhesive tape, adhesive label or shaped diecut.

This planar element is self-adhesive on its first surface and also on its second surface. The first and second surfaces here each correspond to the two surfaces of the planar element parallel to its principal extent, in other words its top face and bottom face.

A surface is termed self-adhesive for the purposes of this specification in particular when it has a self-adhesive on it at least locally, but preferably over a large area or even over the full area. Self-adhesives in the present case include without exception all adhesives based on pressure-sensitive adhesives and/or hotmelt adhesives, in other words adhesives which themselves allow permanent bonding to the substrate. "Based on" or "on the basis of" denotes in the present case that the technical properties of this adhesive system are dependent at least to a large extent on the fundamental properties of this adhesive or these adhesive constituents (referred to as the base polymer), without, of course, ruling out the additional influencing of these properties through use of modifying auxiliaries or additives or of further polymeric adhesives in the adhesive system.

Pressure-sensitive adhesives (PSAs) are adhesives which allow permanent bonding to the substrate at room temperature even under a relatively weak applied pressure. In contrast, hotmelt adhesives are adhesives which enter into a permanent bond with the substrate only at elevated temperatures, the resulting bond being maintained even on subsequent cooling of the bond to room temperature. The bondability of both PSAs and hotmelts derives from their adhesional properties.

Adhesion typically refers to the physical effect brought about by the holding-together of two phases, brought into contact with one another, at their interface on account of intermolecular interactions that occur there. Adhesion therefore defines the attachment of the adhesive to the substrate surface and can be determined as tack and as bond strength. In order to influence the adhesion of an adhesive in a specific way, it is common to add plasticizers and/or bond strength-increasing resins (referred to as tackifiers) to the adhesive.

Cohesion typically refers to the physical effect which results in the internal holding-together of a substance or composition on account of intermolecular and/or intramolecular interactions. The forces of cohesion therefore determine the consistency and fluidity of the adhesive, which can be determined, for instance, as viscosity and as holding power. In order to increase the cohesion of an adhesive in a specific way, it is often subjected to additional crosslinking, for which reactive (and hence crosslinkable) constituents or other chemical crosslinkers are added to the adhesive and/or the adhesive is subjected to actinic (high-energy) radiation in an aftertreatment.

The technical properties of a pressure-sensitive adhesive are determined primarily by the relationship between adhesional and cohesional properties. For certain applications, for example, it is therefore important that the adhesives used are highly cohesive, i.e. possess a particularly strong internal holding-together, whereas for other applications a particularly high adhesion is required.

In accordance with the invention the planar element has a defined layer sequence. A layer sequence is more particularly a spatial arrangement of individual layers which are arranged perpendicular to their principal extent above one another (in stack form) and are each in direct contact with one another without other layers in between. A layer is more particularly a two-dimensional arrangement of a system of unitary functionality whose dimensions in one spatial direction are significantly smaller than in the two other spatial directions which define the principal extent. Such a layer may be of compact or else perforate design, and may be composed of one material or of different materials, particularly when these materials contribute to the unitary functionality of this layer. This layer may have a constant thickness over its whole planar extent, or else different thicknesses. Furthermore, a layer may of course also have more than one single functionality.

Within the layer sequence of the invention there is a contacting layer between a heating layer and an adhesive layer. A contacting layer is any layer which is a good conductor of the electrical current and can be used to apply a voltage to the heating layer and/or to provide passage of a current through the heating layer; the contacting layer serves, accordingly, for the connection of external electrical supply lines to the planar element (contacting electrode function). A heating layer is any layer set up for the heating of the planar element. An adhesive layer is any layer which comprises an adhesive and is adapted for the adhesive joining of the planar element to a substrate. Accordingly the heating layer is in contact with a first side face of the contacting layer (i.e. the top face or the bottom face of the contacting layer) and hence these two layers are in direct—that is, immediate—contact. Moreover, the heating layer is in electrically conducting connection with the first side face of the contacting layer. A connection is termed electrically conducting especially when the overall electrical resistance of the connection, which is made up of the resistances of the sub-sections to be connected and of the contact resistance of the connection, is of a magnitude not more than that of the overall resistances of the remaining conducting regions and contacts.

Furthermore, the second side face of the contacting layer (corresponding to the other side face, i.e. the bottom face or top face of the contacting layer) is in contact with the adhesive layer and contacts it directly. The adhesive layer in this case is composed of a second self-adhesive. Suitable self-adhesives include all customary and suitable pressure-sensitive adhesives and/or hotmelt adhesives.

The heating layer is composed in accordance with the invention, moreover, of an intrinsically heatable first self-adhesive. All customary and suitable PSAs and/or hotmelts are suitable for the first self-adhesive as well. An intrinsically heatable layer is any layer which per se is electrically heatable—in other words, this layer is capable, without further components or parts in the layer, of producing heat itself when an electrical current is passed through the layer or when an electrical voltage is applied to the layer, it being immaterial whether the current or voltage is an alternating current or voltage or else a direct current or voltage. Moreover, the first self-adhesive takes the form of a posistor, which warms up when an electrical current is passed through.

As an element key to the invention, the contacting layer is an at least substantially two-dimensionally extended perforate contacting element. A contacting element is more particularly an element comprising a material that conducts electrical current and whose structure electrically conducts the current continually at least in a sub-region. "At least substantially two-dimensionally extended" means that the sub-regions of which the contacting layer is composed are present within the layer in an areal disposition, it also being possible for individual sub-regions to project out of this areal disposition.

The contacting layer is an electrically conducting connection between the heating layer and the current source or voltage source. In this arrangement the contacting layer may be formed either as one of the two electrode connections (poles) of the heating layer or else may form both electrode connections. Where the contacting layer constitutes only one of the two electrode connections of the heating layer, a second electrode connection is necessary to allow a current to flow through the heating layer and for the heating layer to warm up. In that case this second electrode connection may be formed within the planar element of the invention—in the form of an additional second flexible contacting layer, for instance—or else may be provided on one of the two bonding substrates, for example as a metallic layer on the surface of a glass (for instance, as the silver layer of a mirror).

In accordance with the invention the contacting layer is not closed over its full area but instead is perforate, and so this discontinuous layer has reliefs (depressions) which also extend in a direction perpendicular to the principal extent of the layer. Consequently the layer itself is not compact over its full area, but instead has reliefs which may extend through the layer (continuous holes) or else are limited only to parts of the layer (hollows, for instance for locally reducing the thickness of the contacting layer). The depressions may be of any shape, for instance regular or irregular, of uniform or varying width, and may have upright, oblique or curviform wall sections and the like. The depressions may therefore run in different directions in the contacting layer or else may have one particular preferential direction, and so the contacting layer has a particularly high flexibility transversely to this preferential direction within its principal extent.

With a view to the specific embodiment of these depressions, the contacting element may take different forms, for instance as an interrupted area, as a folded or branched wire structure or the like, for example as a singly or multiply branched comb structure or finger structure. Further suitable contacting elements are, for example, perforate metal foils, expanded metal grids, wire grids, metal meshes or electrically conducting nonwovens. Non-metallic conductors as well such as metal oxides (for example indium tin oxide) or intrinsically conductive polymers can be used in accordance with the invention. To improve the flexibility of the planar element, the at least one contacting layer preferably has an average or even maximum thickness of less than 50 µm, preferably of less than 20 µm or even of less than 10 µm.

The regions of the contacting element that conduct the electrical current may be in conducting connection with one another (all regions or only some of the regions) or may each be present as an individual region of the contacting element which is not in conducting connection with the other regions via the contacting element. Where appropriate it is also possible for some of the regions to be in electrically conducting connection with one another and for other of the regions to be present each individually. This does not of course rule out a conducting connection via the heating layer, which in fact is necessary in accordance with the invention.

Provision is made in particular for the contacting element to comprise two regions which are not in conducting connection with one another and which are designed as the two electrode leads (poles) of the heating layer. Where the whole contacting element is universally conducting, it is used as one of the two poles of the heating layer, in which case a flow of current then occurs through the heating layer principally in a direction perpendicular to the principal extent, whereas, in the case of an arrangement in which the contacting element represents both electrode connections, a lateral flow of current within the principal extent occurs in addition to or instead of the perpendicular flow of current.

As the first self-adhesive of the heating layer it is possible in principle to use all self-adhesives which conduct an electrical current flowing through this self-adhesive, substantially without decomposition. The heat within the self-adhesive heating layer is preferably generated from the drop in voltage in this layer itself that occurs as a result of the electrical resistance, although heating may also be achieved on the basis of other effects, by means, for instance, of another electrothermal transducer or of an electrically initiated exothermic chemical reaction. In accordance with the invention such planar elements may be designed for single or multiple use; likewise, the heat generation process may be able to be carried out once or multiply. A heating layer of this kind may, perpendicular to the principal extent, have an (average) thickness of less than 1 mm, preferably a thickness from a range from 10 µm to 400 µm, more preferably from a range from 20 µm to 200 µm. For the preferred case of a layer which is used as a resistance heater, it may have an electrical resistance which on the one hand is high enough to allow heating of the layer but on the other hand is low enough to establish a flow of current through the layer to start with.

In accordance with the invention this heating layer must also have posistor properties, i.e. have a positive temperature coefficient and hence exhibit a PTC effect. In terms of its positive temperature coefficients and resistance, the layer is preferably designed in such a way that the generation of heat within the heating layer as a result of the PTC effect is limited for the particular operating voltage and the particular operating current, so that the layer is self-regulating with regard to the development of heat, and more particularly does not exceed a defined maximum temperature level. This allows overheating of the planar element to be prevented.

As a first self-adhesive it is preferred here to use a PSA or hotmelt which comprises at least one electrically conductive filler as electrically conductive material. An electrically conductive filler is an admixture to a self-adhesive that conducts electrical current either on its own (i.e. without self-adhesive) or else only in the form of the mixture with the self-adhesive.

As a filler it is possible in principle to use all suitable fillers which are compatible with the first self-adhesive in question. Use is made more particularly for this purpose of fillers selected from the group encompassing graphite and carbon black, more particularly conductive carbon black (for example Printex® XE from Degussa), and also any desired combinations thereof. In addition or instead it is also possible with preference to use other carbon-based fillers, more particularly those which are nanoscale, i.e. have an extent in at least one spatial dimension of not more than 500 nm, preferably of less than 200 nm or even of less than 50 nm, examples being carbon nanoparticles such as carbon nanotubes (for example Carbon Nanotubes from Ahwahnee or Carbon Nanotube Masterbatches from Hyperion Catalysis), carbon nanofibres, fullerenes and the like.

Advantageously the filler is used in an amount such that the fraction of the filler in the first self-adhesive is large enough to ensure sufficient conductivity on the part of the first self-adhesive but on the other hand low enough to have only little adverse effect on the mechanical properties of the first self-adhesive. Furthermore, a combination of different kinds of fillers may also be advantageous, allowing sufficient posistor properties to be achieved in tandom with a very low degree of filler, particularly in the case of the combination of carbon nanotubes with carbon black or graphite.

The fillers may additionally be used in surface-modified form. This allows specific influence to be exerted over particular properties of the first self-adhesive, in order, for instance, to improve the dispersibility of carbon nanotubes or carbon black in the self-adhesive. To increase the PTC effect, the surface of the conductive fillers, such as of the carbon black particles, for instance, may be covered partly or completely with metals such as nickel, silver, or gold, with silanes or with formamides.

Factors governing the conductivity and hence also the attainable temperature and heating rate include the degree of filling of the conductive filler, in other words its mass fraction within the self-adhesive. By raising the degree of filling it is possible to achieve higher conductivities and possibly also higher temperatures. Hence the extent of the effect of the electrical heatability of the first self-adhesive may be determined by the degree of filling. The degree of filling is advantageously between 1% and 60% by weight. Great preference is given to using between 5% and 30% by weight of filler. The electrical conductivity and hence the heatability of the first self-adhesive are also dependent on its base polymer, moreover.

In order to obtain the first self-adhesive with posistor properties, the electrically conductive fillers may be admixed to the monomers of the first self-adhesive prior to the polymerization and/or during the polymerization, and/or may be combined with the polymers only after the end of the polymerization. Preferably the conductive filler is added after the polymerization to a melt of a base polymer of the first self-adhesive.

Particularly when the first self-adhesive is applied from the melt as a hotmelt system to the planar element of the invention, the electrically conductive filler is preferably introduced directly into the melt. In this case its homogeneous incorporation is desirable in the sense of the invention. Homogeneous distributions of the filler in the first self-adhesive are achieved preferably by compounding in twin-screw extruders, continuous compounders (Buss kneaders, for example) or planetary roller extruders. One advantage of this operation is the only brief contamination of the production operation with the separate filler, and also the avoidance of solvents.

As first self-adhesive in the heating layer it is possible in principle to use all polymers having suitable adhesive properties and exhibiting a PTC effect—that is, having posistor behaviour. The occurrence and the extent of a PTC effect are dependent on the formation of a network—for example on whether the conductive filler itself is in agglomerated form or not. The PTC effect here may be assisted by factors, among others, including orientations within the polymeric constituents of the first self-adhesive that are introduced in the course of the production operation, by the introduction, for instance, of an anisotropy with respect to physical properties and/or with respect to the orientation of the macromolecules.

Where a self-adhesive with an electrically conductive filler is used as a system with posistor properties, it has proved to be advantageous to use multi-phase systems, more particularly those in which at least one phase undergoes a volume expansion within the temperature range in which the PTC effect occurs, this volume expansion taking place as a result of the heating and being at least partly responsible, according to generally recognized scientific explanation, for the posistor behaviour (see J. Meyer in Polymer Engineering and Science, 13 (1973), pp. 462-468). Multi-phase systems in the sense of the invention are interpreted as including self-adhesives based on polymers or polymer blends which have one or more further fillers in addition to the conductive filler.

Having emerged as being particularly advantageous in this context is the use of those self-adhesives which have partially crystalline polymers. Partially crystalline polymer systems used may be both single-phase and multi-phase systems, not only homopolymers but also copolymers, especially partially crystalline block copolymers. The partially crystalline polymers may be part of the base polymer itself or else may represent an adjuvant. The crystalline sub-regions of such partially crystalline polymers have a greater thermal expansion when the polymer matrix undergoes softening than do its amorphous regions.

The hotmelt and/or PSA in the heating layer preferably comprises at least 30% by weight of partially crystalline polymers; even better is a fraction of at least 50% by weight of partially crystalline polymers in the self-adhesive. It has been found that in hotmelt adhesives specifically there is a surprisingly sharp increase in the suitability for obtaining the PTC effect as the fraction of partially crystalline polymers goes up. PSAs, in contrast, lose their pressure-sensitive adhesive properties as the partially crystalline fraction goes up, and so, when using PSAs, the fraction of partially crystalline polymers should be kept lower than in the case of hotmelts, in order to ensure a sufficiently high pressure-sensitive adhesiveness.

Hotmelt adhesives, consequently, are highly suitable beyond expectations for the utilization of the PTC effect. Having emerged as being particularly advantageous in the sense of the invention in this context as a first self-adhesive are hotmelt adhesives comprising partially crystalline polymers which are present at 100% by weight in the base polymer of the adhesive or which are present at least nearly 100% by weight in the adhesive.

In a hotmelt adhesive and/or pressure-sensitive adhesive as first self-adhesive, particularly advantageous partially crystalline polymers are those in which the degree of crystallinity is more than 20% or even more than 40%. The degree of crystallinity can be determined with the aid of dynamic differential calorimetry (Differential Scanning Calorimetry; DSC).

Thus as a first self-adhesive it is possible, in the range of partially crystalline thermoplastics, to use polyolefins (low density polyethylene, for example) or copolymers of polyolefins (ethylene-vinyl acetate (EVA), ethylene-acrylic acid (EAA), ethylene-methacrylic acid (EMAA), ethylene-ethyl acrylate or ethylene-butyl acrylate, for example), ionomers, polyamides and/or their copolymers. As well as a sufficiently pronounced PTC effect, these substances also have particularly advantageous hotmelt adhesive properties, and so can be used as a base polymer for a first self-adhesive based on a hotmelt adhesive.

Additionally preferred in the range of partially crystalline thermoplastics are acid-modified (with maleic acid or maleic anhydride, for example) polyolefins or their copolymers, since their compatibility with the conductive fillers such as, for instance, carbon black or carbon nanotubes is especially good and since when these polymers are used it is particularly easy to prepare homogeneous dispersions of the filler in the polymer matrix.

Very particularly preferred block copolymers used are styrene block copolymers such as, for instance, SBS (styrene-butadiene-styrene block copolymers), SIS (styrene-isoprene-styrene block copolymers), SEBS (styrene-ethylene-butylene-styrene-block copolymers) or SEPS (styrene-ethylene-propylene-styrene block copolymers).

Also advantageous is the addition of polymeric or inorganic fillers which support the PTC effect by melting in the course of heating. These may be, for example, highly crystalline polyolefin waxes or ionic liquids (low-melting metal salts). The choice of the melting point of the fillers also allows the temperature at which a posistor behaviour (PTC effect) occurs to be adjusted.

In accordance with the invention either one of the two self-adhesives or else both self-adhesives may be pressure-sensitive adhesives (PSAs). Instead it is also possible for one of the two self-adhesives or else for both self-adhesives to be hotmelt adhesives. In this case it is of course also possible for one of the two adhesives to be a PSA and the other to be a hotmelt, in other words either for the first self-adhesive to be a PSA and the second self-adhesive a hotmelt or for the first self-adhesive to be a hotmelt and the second self-adhesive a PSA.

Suitable PSAs include in principle all PSA systems having suitable pressure-sensitive adhesive properties, in other words pressure-sensitively adhesive systems. The monomers that serve for preparing the PSAs are selected more particularly in such a way that the resulting polymers can be used as PSAs at room temperature or higher temperatures.

An adhesive is pressure-sensitively adhesive in the sense of the present invention if it possesses pressure-sensitive adhesive properties in accordance with the "Handbook of Pressure Sensitive Adhesive Technology" by Donatas Satas (van Nostrand, New York 1989).

In order to achieve a polymer glass transition temperature, $T_g$, of $T_g \leq 25°$ C., which is preferred for PSAs, the monomers are typically selected such, and the quantitative composition of the monomer mixture selected such, that they behave in such a way, in analogy to the equation presented by Fox (cf. T. G. Fox, Bull. Am. Phys. Soc. 1 (1956) 123), that the desired value for the glass transition temperature $T_g$ of the resulting polymer is given by $$\frac{1}{T_g} = \sum_n \frac{w_n}{T_{g,n}} \quad (E1)$$

In this equation, n represents the serial number of the monomers used, $w_n$ the mass fraction of the respective monomer n (% by weight) and $T_{g,n}$ the respective glass transition temperature of the homopolymer of the respective monomers n, in K.

Examples of PSAs suitable for the first self-adhesive and/or the second self-adhesive are therefore PSAs based on acrylates and/or methacrylates, natural rubbers and/or synthetic rubbers.

Therefore it is possible to use PSAs based on acrylic acid and/or methacrylic acid and/or based on esters of the aforementioned compounds, or those based on hydrogenated natural or synthetic rubbers, on account of their particular ageing stability and hence their capacity to withstand repeated heating operations of the planar element of the invention over a long time.

Suitable more particularly are acrylate PSAs which are obtainable, for instance, by free-radical addition polymerization and which are based at least partly on at least one acrylic monomer of the general formula $CH_2=C(R^1)(COOR^2)$, where $R^1$ is H or a $CH_3$ radical and $R^2$ is H or is selected from the group consisting of saturated, unbranched and branched, substituted and unsubstituted $C_1$ to $C_{30}$ alkyl radicals. The at least one acrylic monomer ought to have a mass fraction of at least 50% by weight in the PSA.

According to one particularly advantageous embodiment it is possible further to use polymers which (a1) are based at least partly on at least one acrylic monomer of the general formula $CH_2=C(R^1)(COOR^{2'})$, where $R^1$ is H or a $CH_3$ radical and $R^{2'}$ is selected from the group consisting of saturated, unbranched and branched, substituted and unsubstituted $C_2$ to $C_{20}$ alkyl radicals, and (a2) are based at least partly on a comonomer which is polymerizable with the at least one acrylic monomer and may be selected in particular from vinyl compounds having functional groups, maleic anhydride, styrene, styrene compounds, vinyl acetate, acrylamides, and photoinitiators functionalized with a double bond.

Preferably the at least one acrylic monomer (a1) here has a mass fraction of 65% to 100% by weight and the at least one comonomer (a2) has a mass fraction of 0% to 35% by weight in the self-adhesive.

Furthermore, an average molecular mass $M_w$ (weight average) of the self-adhesive of not more than 800 000 g/mol has proved to be advantageous, particularly with regard to the desired mechanical properties of the PSA.

According to a further embodiment the at least one self-adhesive may also comprise or be based on natural or synthetic rubber compositions. For self-adhesives comprising natural rubber, the natural rubber is ground to a freely selectable molecular weight and then additized with the electrically conductive filler.

As one particular embodiment for this purpose it is also possible for partially crystalline polymers such as EVA (ethylene-vinyl acetate) or polyolefins to be used as the self-adhesive or to be added thereto. More particularly, in the case of use as a first self-adhesive, these adhesive systems offer an additional assistance to the PTC effect, owing to the increase in volume of the crystalline phase that occurs therein when the crystallite melting temperature is exceeded.

It is preferred to use acrylic or methacrylic monomers of the general formula $CH_2=C(R^1)(COOR^{2''})$ which comprise acrylic and methacrylic esters, the group $R^{2''}$ being selected from the group consisting of saturated, unbranched and branched, substituted and unsubstituted $C_4$ to $C_{14}$ alkyl radicals, more particularly $C_4$ to $C_9$ alkyl radicals. Specific examples, without wishing to be restricted by this enumeration, are methyl acrylate, methyl methacrylate, ethyl acrylate, n-butyl acrylate, n-butyl methacrylate, n-pentyl acrylate, n-hexyl acrylate, n-heptyl acrylate, n-octyl acrylate, n-octyl methacrylate, n-nonyl acrylate, lauryl acrylate, stearyl acrylate, behenyl acrylate and their branched isomers, examples being isobutyl acrylate, 2-ethylhexyl acrylate, 2-ethylhexyl methacrylate, isooctyl acrylate or isooctyl methacrylate.

Further classes of compound which can be used are monofunctional acrylates and/or methacrylates of the general formula $CH_2=C(R^1)(COOR^{2'''})$, the radical $R^{2'''}$ being selected from the group of bridged and unbridged cycloalkyl radicals having at least 6 C atoms. The cycloalkyl radicals may also be substituted, for example by $C_1$ to $C_6$ alkyl groups, halogen atoms or cyano groups. Specific examples are cyclohexyl methacrylate, isobornyl acrylate, isobornyl methacrylate and 3,5-dimethyladamantyl acrylate.

In one preferred procedure, acrylic monomers and/or comonomers are used which contain one or more substituents, more particularly polar substituents, examples being carboxyl, sulphonic acid, phosphonic acid, hydroxyl, lactam, lactone, N-substituted amide, N-substituted amine, carbamate, epoxy, thiol, alkoxy, cyano, halide and ether groups.

Suitable with great advantage in the sense of acrylic monomers (a1) are monomers which are selected from the following group: substituted and unsubstituted compounds encompassing methyl acrylate, methyl methacrylate, ethyl acrylate, n-butyl acrylate, n-butyl methacrylate, n-pentyl acrylate, n-hexyl acrylate, n-heptyl acrylate, n-octyl acrylate, n-octyl methacrylate, n-nonyl acrylate, lauryl acrylate, stearyl acrylate, behenyl acrylate, isobutyl acrylate, 2-ethylhexyl acrylate, 2-ethylhexyl methacrylate, isooctyl acrylate, isooctyl methacrylate, cyclohexyl methacrylate, isobornyl acrylate, isobornyl methacrylate and 3,5-dimethyladamantyl acrylate.

Likewise suitable are moderately basic comonomers (a2) such as singly or doubly N-alkyl-substituted amides, more particularly acrylamides. Specific examples here are N,N-dimethylacrylamide, N,N-dimethylmethacrylamide, N-tert-butylacrylamide, N-vinylpyrrolidone, N-vinyllactam, dimethylaminoethyl acrylate, dimethylaminoethyl methacrylate, diethylaminoethyl acrylate, diethylaminoethyl methacrylate, N-methylolacrylamide, N-methylolm ethacrylamide, N-(butoxymethyl) methacrylamide, N-(ethoxymethyl)acrylamide, N-isopropylacrylamide, this enumeration as well not being conclusive.

Further preferred examples of comonomers (a2) are hydroxyethyl acrylate, hydroxyethyl methacrylate, hydroxypropyl acrylate, hydroxypropyl methacrylate, allyl alcohol, maleic anhydride, itaconic anhydride, itaconic acid, glycerldyl methacrylate, phenoxyethyl acrylate, phenoxyethyl methacrylate, 2-butoxyethyl acrylate, 2-butoxyethyl methacrylate, cyanoethyl acrylate, cyanoethyl methacrylate, glyceryl methacrylate, 6-hydroxyhexyl methacrylate, vinylacetic acid, tetrahydrofurfuryl acrylate, beta-acryloyloxypropionic acid, trichloroacrylic acid, fumaric acid, crotonic acid, aconitic acid, dimethylacrylic acid, this enumeration not being conclusive.

In a further preferred procedure, use is made as comonomers (a2) of vinyl compounds, more particularly vinyl esters, vinyl ethers, vinyl halides, vinylidene halides, vinyl compounds with aromatic rings and heterocycles in alpha position, examples that may be mentioned including—not exclusively—vinyl acetate, vinylformamide, vinylpyridine, ethyl vinyl ether, vinyl chloride, vinylidene chloride, styrene and acrylonitrile, for instance.

With particular advantage the at least one comonomer (a2) may be a photoinitiator having a copolymerizable double bond, selected more particularly from the group containing Norrish I photoinitiators or Norrish II photoinitiators, benzoin acrylates or acrylated benzophenones.

In a further preferred procedure, the comonomers (a2) described are admixed with additional monomers which possess a high static glass transition temperature. Suitable such additional monomers include aromatic vinyl compounds such as, for instance, styrene, in which case preferably the aromatic rings are composed of $C_4$ to $C_{18}$ units and can also contain heteroatoms. Particularly preferred examples are 4-vinylpyridine, N-vinylphthalimide, methylstyrene, 3,4-dimethoxystyrene, 4-vinylbenzoic acid, benzyl acrylate, benzyl methacrylate, phenyl acrylate, phenyl methacrylate, tert-butylphenyl acrylate, tert-butylphenyl methacrylate, 4-biphenyl acrylate and 4-biphenyl methacrylate, 2-naphthyl acrylate and 2-naphthyl methacrylate, and also mixtures of these monomers, this enumeration again being not conclusive.

Suitable hotmelt adhesives include in principle all hotmelt adhesive systems having suitable hotmelt-adhesive properties, in other words systems with hotmelt tack. A planar element with hotmelt tack for the purposes of the present invention is a planar element of the invention where, following application in melt form to the substrate and subsequent cooling, the bond strength at room temperature in accordance with ASTM D 3330-04 (with a removal speed of 300 mm/min on the bond substrate) is greater than 1 N/cm, more particularly greater than 3 N/cm or even greater than 5 N/cm.

Instead of or in addition to PSAs, therefore, the planar element of the invention may comprise hotmelt adhesives for the first self-adhesive and/or for the second self-adhesive. Hotmelt adhesives which can be used are all customary and suitable hotmelt adhesives, examples being those based on synthetic rubbers, on thermoplastic materials, on elastomers with modifier resins, on acrylic acid derivative-vinyl copolymers and on acrylate-containing block copolymers.

Of these adhesives, those which have emerged as being advantageous are, in particular, those from the group encompassing polyolefins and copolymers of polyolefins and also their acid-modified derivatives, ionomers, polyamides and their copolymers, and also block copolymers such as styrene block copolymers, reference being made first to the above-described partially crystalline adhesives. Such adhesives may of course also be employed here for the second self-adhesive.

The self-adhesives used for the planar elements of the invention are preferably additionally crosslinked, the aim being to achieve high degrees of crosslinking, which have the effect in particular, among others, of boosting the PTC effect (compare EP 0 311 142 A1 and also U.S. Pat. No. 4,775,778 A) and are therefore especially suitable for the first self-adhesive. Crosslinking also eliminates or reduces the consequences of the NTC (Negative Temperature Coefficient) effect, which is occasionally observed at temperatures above the melting point of the first self-adhesive.

According to one preferred embodiment of the invention a base polymer of the first self-adhesive preferably has a degree of crosslinking which corresponds at least to a gel value of 35%, more particularly of more than 60%. The gel value in the present case is the proportion of the fractions of a base polymer that are not soluble in a suitable solvent (toluene or xylene, for example) to the sum of soluble fractions and non-soluble fractions of the base polymer.

A high degree of crosslinking may be obtained, for instance, in a crosslinking step with electron beams. Typical irradiation equipment that may be employed encompasses linear cathode systems, scanning systems (scanner systems) or segmented cathode systems, provided that these are electron beam accelerators. A comprehensive description of the state of the art, and the most important process parameters, are found in Skelhorne, "Electron Beam Processing", in "Chemistry and Technology of UV and EB Formulation for Coatings, Inks and Paints", Vol. 1, 1991, SITA, London. Typical acceleration voltages are situated in the range between 50 kV and 500 kV, preferably in the range between 80 kV and 300 kV. The radiation doses employed range between 5 kGy to 150 kGy, more particularly between 20 kGy and 100 kGy. It is also possible to use other processes which allow high-energy irradiation.

A further possibility, in accordance with the invention, is to bring about a variation in the electrical conductivity and hence in the thermal heating via the degree of crosslinking. By raising the electron beam dose that is active in a crosslinking reaction (and consequently raising the degree of crosslinking) it is possible to raise the electrical conductivity, so that, with a constant flow of current through the heating layer of the planar element, there is an increase in the attainable temperature of the self-adhesive. It is likewise possible to control the posistor behaviour of the first self-adhesive via the degree of crosslinking.

To reduce the radiation dose needed for a crosslinking reaction it is additionally possible to admix the self-adhesive with crosslinkers and/or crosslinking promoters, more particularly those which are excitable thermally or by means of electron beams. Suitable crosslinkers for electron beam crosslinking include, for instance, difunctional or polyfunctional acrylates or methacrylates, or triallyl cyanurates and triallyl isocyanurates. Thermally activable crosslinkers admixed are preferably difunctional or polyfunctional epoxides, hydroxides, isocyanates or silanes.

An adhesive may of course comprise further formulating ingredients and/or adjuvants such as, for example, auxiliaries, pigments, rheological additives, adhesion promoter additives, plasticizers, resins, elastomers, ageing inhibitors (antioxidants), light stabilizers, UV absorbers and also other auxiliaries and additives, examples being driers (for instance, molecular sieve zeolites or calcium oxide), flow agents and flow control agents, wetters such as surfactants or catalysts and also thermally conducting fillers, heat-storing fillers or adjuvants which are released by heat or whose release is supported by heat.

Auxiliaries which can be used are all finely ground solid additives such as, for example, chalks, magnesium carbonate, zinc carbonate, kaolin, barium sulphate, titanium dioxide or calcium oxide. Further examples are talc, mica, silica, silicates or zinc oxide. Mixtures of the substances stated may of course also be used.

The pigments employed may be organic or inorganic in nature. All kinds of organic or inorganic colour pigments are suitable, examples being white pigments such as titanium dioxide, for improving the light stability and UV stability, or metal pigments.

Examples of rheological additives are fumed silicas, phyllosilicates (bentonites, for example), high molecular mass polyamide powders or powders based on castor oil derivatives.

Possible examples of adhesion promoter additives include substances from the groups of the polyamides, epoxides or silanes.

Examples of plasticizers for enhancing the adhesion capacity are phthalic esters, trimellitic esters, phosphoric esters, adipic esters and esters of other acyclic dicarboxylic acids, fatty acid esters, hydroxycarboxylic esters, alkylsulphonic esters of phenol, aliphatic, cycloaliphatic and aromatic mineral oils, hydrocarbons, liquid or semi-solid rubbers (for example nitrile rubbers or polyisoprene rubbers), liquid or semi-solid polymers of butene and/or isobutene, acrylic esters, polyvinyl ethers, liquid resins and plasticizer resins based on the raw materials that also constitute the basis for tackifying resins, woolwax and other waxes, silicones and also polymer plasticizers such as polyesters or polyurethanes, for instance.

Adjuvants which are released by heat or whose release is supported by heat are those systems which include an active substance which, as a result of exposure to heat, is released or activated, thereby allowing controlled delivery of this active substance. A suitable active substance in this context is any substance which develops a particular activity on thermal release or activation: for example, a dye, an active medical or cosmetic substance or a detonator (initial explosive). The activity may begin, for instance, as a result of the release of the substance (as in the case of a topically appliable active substance, for example) or on thermal activation, for instance a thermally initiated chemical reaction (for example, a molecular rearrangement, a crosslinking reaction or a decomposition) or a thermally initiated physical process (for example, an adsorption/desorption or a phase transition). The adjuvant which can be released by heat may be, for example, a topically appliable active medical substance which is encapsulated in a meltable matrix.

The formulating of the adhesive with further constituents such as auxiliaries and plasticizers, for example, is likewise state of the art.

To optimize the technical properties it is possible to admix the self-adhesives of the invention with resins. Tackifying resins (bond strength enhancer resins) that can be used for addition include, without exception, all of the known tackifier resins described in the literature. Representatives include the pinene resins, indene resins and rosins, their disproportionated, hydrogenated, polymerized and esterified derivatives and salts, the aliphatic and aromatic hydrocarbon resins, terpene resins and terpene-phenolic resins, and also $C_5$ to $C_9$ and other hydrocarbon resins. Any desired combinations of these and additional resins may be used in order to adjust the properties of the resultant adhesive in accordance with requirements. Generally speaking, it is possible to use all resins that are compatible (soluble) with the corresponding base polymer; reference may be made more particularly to all aliphatic, aromatic and alkylaromatic hydrocarbon resins, hydrocarbon resins based on pure monomers, hydrogenated hydrocarbon resins, functional hydrocarbon resins and natural resins. One preferred version uses resins which do not reduce the electrical conductivity and the heatability, even over a prolonged period of time.

A further advantageous embodiment of the planar element can be achieved by adding a heat-storing filler to at least one of the layers. A heat-storing filler is understood in the present case to be any filler having a high heat capacity, more particularly having a heat capacity of more than 0.7 J/gK. As a result of the thermal buffer effect of these substances, it is possible in this way to achieve a uniform profile on heating and also a prolonged and uniform delivery of heat after the end of the active process of heat generation. Fillers with a high heat capacity that can be used with advantage include, for instance, aluminium, beryllium, boron, calcium, iron, graphite, potassium, copper, magnesium, phosphorus or compounds of the aforementioned substances, especially aluminium oxide and aluminium chloride, calcium carbonate, calcium chloride, copper sulphate, magnetite, haematite, magnesium carbonate and magnesium chloride, phosphorus chloride or phosphorus oxide (it also being possible for these substances, furthermore, to fulfil further functions within the planar element, such as potassium or phosphorus in the case of detonators).

It is also advantageous if at least one of the self-adhesive layers has a high thermal conductivity, more particularly of at least 0.5 W/m·K, very preferably of more than 1 W/m·K. This can be achieved, for instance, by addition of thermally conducting fillers, especially of electrically insulating but highly thermally conducting fillers such as, for instance, boron nitride or aluminium oxide, since the latter do not affect the electrical properties. It is, however, also possible to use electrically conductive fillers with a high thermal conductivity, examples being silver, aluminium or copper. PSAs with particular thermal conductivity allow the energy that is needed to melt a hotmelt to be introduced more effectively, leading, for instance, to shortened cycle times when the planar element of the invention is applied to the bonding substrate.

In accordance with the invention the composition of the first self-adhesive may be identical to or different from the composition of the second self-adhesive.

In addition to the heating layer, the contacting layer and the adhesive layer, the planar element of the invention may have further layers. Thus, for instance, it is possible for the planar element to comprise further layers of adhesives, by the provision, for instance, of a third self-adhesive on the side face of the heating layer that faces away from the perforate contacting element. This adhesive as well may be any suitable pressure-sensitive adhesive or hotmelt adhesive: for example, a self-adhesive with one of the base adhesives described above.

In a further advantageous embodiment at least one layer of the heatable planar element is equipped with a mechanism which on first heating of the planar element leads to an increase in cohesion in the first self-adhesive, in the second self-adhesive and/or, where appropriate, in the third self-adhesive. This may be achieved, for example, via an increase in the crosslinking density as a result of a thermally initiated post-crosslinking, which may be initiated in particular by the (intrinsic) heating of the planar element itself. Advantageously, therefore, a planar element of this kind is used in such a way that first the bond with at least one bonding substrate is produced and then the first heating is performed, in the course of which there is a solidification of the bond.

The planar element is typically of backing-free form, since this ensures maximum flexibility of the planar element overall. Furthermore, however, there may also be a flexible permanent backing in the planar element. This backing may be used, for instance, to achieve an overall improvement in the mechanical properties of the planar element, such as its puncture resistance, for example. As permanent backings of this kind it is possible to use all suitable backing materials, such as foils of metal and/or films of plastics, textile planar elements (for example woven, laid, knitted and nonwoven fabrics) or combinations of such materials. These permanent backings as well may be closed over their full area or of perforate design. Where a permanent backing of this kind is provided, however, it is necessary in accordance with the invention that it is not in direct contact with the contacting element but is instead arranged at most on one of the self-adhesive layers.

It is advantageous in this case if the permanent backing as well, in addition to its high flexibility, has a high thermal conductivity, more particularly a thermal conductivity of at least 0.5 W/m·K or even of more than 1 W/m·K. Particularly preferred materials are polymers filled with thermally conductive fillers such as boron nitride or aluminium oxide. Permanent backings of this kind typically have a thickness of less than 50 µm, preferably of less than 25 µm, in order not to detract from the flexibility of the construction as a whole. Through particularly thermally conductive backings it is possible more effectively to introduce the energy that is needed to melt a hotmelt adhesive, resulting, for instance, in short cycle times when the planar element of the invention is applied to the bonding substrate. In one particularly advantageous embodiment the permanent backing takes the form of a polymeric foam, since this does not substantially detract from the flexibility of the planar element as a whole.

The planar element may further have a temporary backing on its first self-adhesive side face and/or on its second self-adhesive side face. As a temporary backing of this kind it is possible to use any release-effect liner material, such as a release paper or an in-process liner, which at least partly covers one of the outer self-adhesives. Examples of suitable liner material include all siliconized or fluorinated films having a release effect which are residuelessly redetachable. Film materials that may be mentioned here include, only by way of example, PP (polypropylene), BOPP (biaxially oriented polypropylene), MOPP (monoaxially oriented polypropylene), PET (polyethylene terephthalate), PVC (polyvinyl chloride), PU (polyurethane), PE (polyethylene), PE/EVA (polyethylene-ethylene-vinyl acetate copolymers) and EPDM (ethene-propylene-diene terpolymers). It is also possible, moreover, to use release papers, examples being glassine papers, kraft papers or polyolefinically coated papers.

Particular advantage attaches to using liner materials which themselves have a high thermal conductivity, more particularly a thermal conductivity of at least 0.5 W/m·K or even of more than 1 W/m·K. Particularly preferred materials are polymers filled with thermally conductive fillers such as boron nitride or aluminium oxide. Through particularly thermally conductive liner materials it is possible more effectively to introduce the energy that is needed to melt a hotmelt adhesive, resulting, for instance, in short cycle times when the planar element of the invention is applied to the bonding substrate.

The planar element accordingly comprises at least one layer within which heat can be generated, this layer being pressure-sensitively adhesive or hotmelt-adhesive; at least one further layer, which is pressure-sensitively adhesive or hotmelt-adhesive; and also—between these layers—a discontinuous electrically conductive layer which constitutes at least one electrode (one pole) of the contacting layer. It is important here that the contacting element is not applied to a backing layer but is instead disposed directly between the heating layer and the adhesive layer.

For producing the planar elements of the invention it is possible without exception to employ all known and suitable methods. Thus the polymeric pressure-sensitive adhesive layers or hotmelt-adhesive layers of the planar element of the invention can be produced by the familiar methods of producing polymeric planar elements in accordance with the prior art. These include, for instance, flat film extrusion, blown film extrusion, the calender method, and coating from a solution, from a dispersion or from a monomeric or prepolymeric precursor of the polymer.

To produce the planar elements, customarily one of the two self-adhesives is first spread out in the form of a stratum, on a permanent backing or on a production backing—a so-called in-process liner—for instance, which is separated from the planar element again during the process or by no later than the end of the process. The contacting element is applied on top of this self-adhesive layer. Following the application of the contacting element, the other self-adhesive is applied to the free side face of the contacting element.

It is of course also possible to obtain the planar element of the invention in any other production method that deviates from the one above; for example, by first applying the contacting element to an in-process liner, then joining it with one self-adhesive, removing the in-process liner from the contacting element, and applying the other self-adhesive to the now free side face of the contacting element.

To apply the contacting element to one self-adhesive or, where appropriate, to the in-process liner it is possible to use all of the known methods, such as the application (printing, for example) of conductive varnishes, conductive pastes or conductive inks, transfer from metal sheets, foils or layers (those made of metals, for example) by means of hot stamping, heat sealing, laminative application or discontinuous application of mixtures of polymers and conductive fillers (polymer/carbon black compounds, for example), it being necessary in the latter case for the contacting element to have a conductivity which is higher by a factor of at least 10 than the conductivity of the intrinsically heatable first self-adhesive.

In one simple embodiment of such a method the heatable first self-adhesive is contacted with an electrically conductive metal grid. In a preferred way, metals are used which exhibit little or no corrosion over a relatively long period of time. One very preferred embodiment, for example, uses copper or aluminium, although contacting may also be performed using silver or gold.

In one preferred embodiment the metal can be deposited directly on the self-adhesive, by electroplating or vapour deposition methods, for instance, or by laser methods, or else may be laminated on in the form of a continuous or perforate layer, by being transferred from an in-process liner.

Where conductive varnish, a conductive ink, a conductive printing ink, an intrinsically conductive polymer or a polymer/conductive substance mixture is used, preference is given to printing methods, particularly, for instance, to screen printing, since in this way the discontinuous contacting layers can be applied particularly easily, variably and reproducibly. Printing may in this case take place from a solution, from a dispersion or from a melt.

In the context of the production of the planar element of the invention it may be particularly advantageous to carry out this production in accordance with a method in which first of all a first adhesive coating is produced from one of the two self-adhesives (for instance by applying the adhesive to an in-process liner) and in which the perforate contacting element is then applied directly to the top face of the resulting stratum, it being possible, where appropriate, for this to take place under applied pressure, and in which, finally, the second adhesive coating of the other self-adhesive is applied to the surface of the perforate contacting element.

In accordance with the invention the planar elements are used for connecting two bonding substrates to one another or else for connecting two different sub-regions of a single bonding substrate. Since the planar element is of double-sided self-adhesive form, it is adapted for adhesively connecting the surfaces of two bonding substrates to one another. More particularly the planar element finds application for the bonding of bonding substrates in the vehicle industry, and is used, for instance, in cars, buses, railways, boats or aircraft.

The planar element of the invention may be present as part of an adhesively bonded assembly. An adhesively bonded assembly for the present purposes is any assembly, obtained by means of adhesive bonding, of a planar element and at least one bonding substrate which is bonded either to the first self-adhesive side face or to the second self-adhesive side face of the planar element directly or via further parts. As a bonding substrate it is advantageous to use a mirror sheet, more particularly the reverse of the mirrored side of a mirror sheet, or, in the case of a transparent planar element, a viewing sheet, such as a display window or a windscreen, for example. Accordingly the planar element of the invention is used for heating an adhesively bonded assembly of this kind.

Thus the planar element of the invention can be used, for instance, as a mirror heater (exterior and interior mirrors), in a heatable inner liner (fastening, sound damping, heating), for heating screenwash or providing an anti-freeze function, for tank heating (especially for diesel vehicles), for the heating of fuel lines (at the same time as fastening), in a heater for deicing systems (wing deicing, possibly including fastening functions), in a steering wheel heater, for warming heating air (additional heating when an engine is cold) or for preheating intake air (combustion air). This list is purely exemplary, and the application of the planar element of the invention is not restricted solely to these specific examples.

Furthermore there are a multiplicity of other applications that can be found, for example (without imposing any restriction as a result of this selection): for preventing condensation or misting on surfaces (for example in the case of bathroom mirrors, for fastening and heating, as an anti-mist lamination for bathroom applications, for instance, or as a heatable tile adhesive sheet, on corrective spectacles or sunglasses or in spectacle cases), as seat heating (in cars, for example, including the integrated application of seat heating and seat occupancy sensor for airbags), for seating at bus stops, in sports stadiums, in outdoor catering or for toilet seats, in electric overblankets or underblankets, in plates for keeping things warm (such as for foods and meals, but also in mountaineering cookers or mountaineering ovens, especially in association with the use of solar cells), in footwear warmers (as an insole, for instance), in band heaters (for pipelines, tanks and the like, for instance), for room heating (for example in wall heaters, floor heaters or else as a foldable tent heater), in water-bed heaters, in heatable housings (for example as a so-called thermobox for conditioning the temperature of the contents of the casing, or in the electronics sector, for instance in interaction with a Peltier element in HiFi equipment, for ensuring a constant temperature), for motorcycles (for example as stirrer heating or saddle heating), as greenhouse heating (for example as large-area radiant heating or convection heating or as small-area local heating directly to the plants, for instance as root heating), for functionally heatable clothing (for example in motorcycle rider clothing, car driver clothing or winter clothing), for heating and, where appropriate, fastening of display systems (for example of LCDs, OLEDs and electrophoretic displays, for instance as anti-freeze protection for displays in cameras or outdoor displays, or in church tower clocks, for instance for their deicing), for heating heated exterior switches, for roof heating (for example as a thawing unit for roofs or gutters), incubators (for example for young animals, for egg hatching or for human babies), in medical therapy (for example in thermotherapy, as heating patches and also for transdermal therapeutic systems and for transdermal drug delivery) or as detonators.

In accordance with the particular self-adhesive used, the planar element is fixed merely under applied pressure to the bonding substrate (in the case of a pressure-sensitive adhesive) or else is fixed to the bonding substrate under applied pressure with introduction of heat (in the case of a hotmelt adhesive). This introduction of heat takes place from the outside; alternatively, however, the heat needed to obtain a stable bond can also be generated intrinsically in the heating layer.

Further advantages and application possibilities will become apparent from the working examples, which are to be described in more detail below with reference to the attached drawings. In those drawings FIG. 1 shows in the upper part a schematic representation of a longitudinal section through an inventive planar element having a perforate contacting element with comb structure, in which all of the sub-regions are in electrically conducting connection to one another through the perforate contacting element; in the middle part, a schematic representation of a horizontal section over the above planar element; and, in the bottom part, a schematic representation of a longitudinal section through the inventive planar element in the bonded state on a top substrate and a bottom substrate with a counterelectrode;

Each of the planar elements described exemplarily below has a heatable first self-adhesive 10, a contacting element 20 and a second self-adhesive 30.

Figure 1:
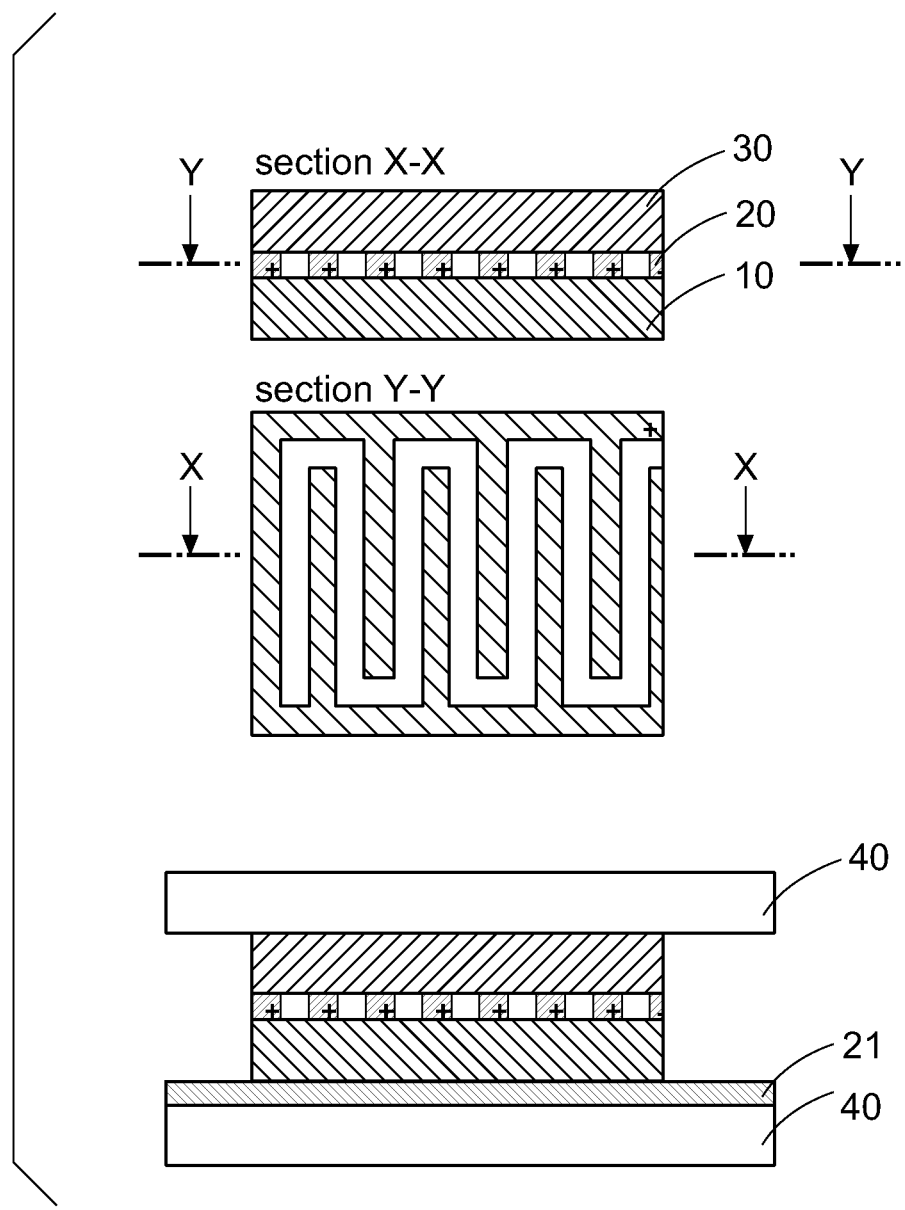

FIG. 1 depicts an inventive planar element having a first self-adhesive 10, a contacting element 20 and a second self-adhesive 30. This planar element does not have a stabilizing backing film that lowers the flexibility. The first self-adhesive 10 and the second self-adhesive 30 are each either pressure-sensitively adhesive or hotmelt-adhesive. Within the first self-adhesive 10, as heating layer, heat is generated on the flow of a current. Arranged between the adhesive strata, the contacting element 20 serves as a discontinuous electrically conductive layer of the contacting of the first self-adhesive 10.

The contacting element 20 here has a comb structure of uniform cross-section in which the fingers in the upper sub-region branch off on the same side of the main strand as the fingers in the lower sub-region. As can be seen from the middle part of FIG. 1, all of the sub-regions of the contacting element 20 are connected universally to one another, and so said element in the layer is able to serve as a single contacting electrode (pole) of the intrinsically heatable first self-adhesive (represented by the—arbitrarily selected—symbol "+"). In association with the bonding substrates 40, therefore, a further contacting electrode is necessary as an external counterelectrode 21, to allow a current to flow through the first self-adhesive layer. In the present case this external counterelectrode is applied as a thin metallic layer on the top face of the lower bonding substrate 40. In interaction between contacting element 20 and external counterelectrode 21, a flow of current is possible through the first self-adhesive, and runs substantially perpendicular to the two-dimensional extent of the first self-adhesive (i.e. in the z direction).

Figure 2:
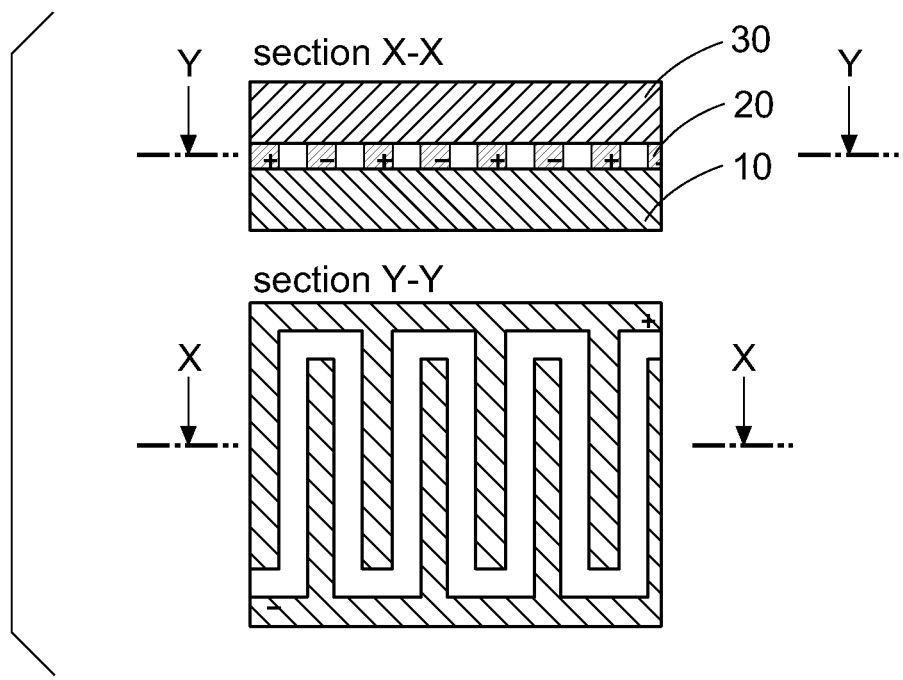
FIG. 2 shows in the top part a schematic representation of a longitudinal section through an inventive planar element having a perforate contacting element with dual comb structure, in which two sub-regions are not in electrically conducting connection via the perforate contacting element; and in the bottom part a schematic representation of a horizontal section through the above planar element.

FIG. 2 depicts a further inventive planar element having a first self-adhesive 10, a contacting element 20 and a second self-adhesive 30. Here again, the first self-adhesive 10 and the second self-adhesive 30 are each either pressure-sensitively adhesive or hotmelt-adhesive. Within the first self-adhesive 10, as a heating layer, heat is generated on the flow of a current. Arranged between the adhesive strata, the contacting element 20 serves as a discontinuous electrically conductive layer of the contacting of the first self-adhesive 10.

Here again, the contacting element 20 has a comb structure of uniform cross-section. As can be seen from the bottom part of FIG. 2, the top sub-region of the contacting element 20 and the bottom sub-region of the contacting element 20, however, are not connected to one another universally, and so each of the two sub-regions is able to serve itself as a contacting electrode of the intrinsically heatable first self-adhesive, and the contacting element therefore contains both contacting electrodes (represented by the—arbitrarily selected—different symbols "+" and "−"), which is why there is no need for an external counterelectrode. In interaction between the two sub-regions of the contacting element 20, there is a flow of current through the first self-adhesive, which runs substantially within the plane of the two-dimensional extent of the first self-adhesive (i.e. in the xy plane) and only a little perpendicular to that plane.

Figure 3:
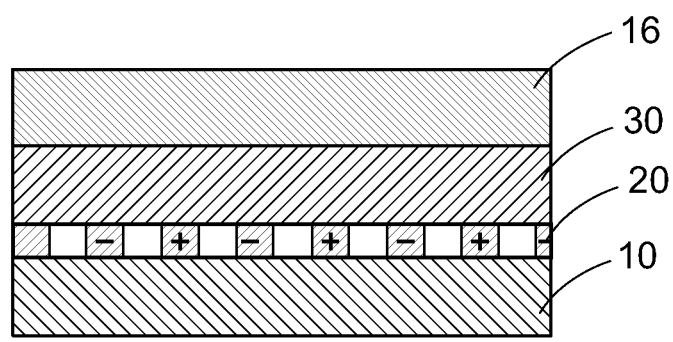
FIG. 3 shows a schematic representation of a longitudinal section through an inventive planar element having a perforate contacting element with dual comb structure and having a permanent backing as bonding substrate.

The planar element depicted in FIG. 3 is identical to the planar element depicted in FIG. 2 in terms of the design and arrangement of the first self-adhesive 10, the contacting element 20 and the second self-adhesive 30. In contrast to the construction depicted in FIG. 2, however, the planar element depicted in FIG. 3 has a permanent backing 16 which is arranged as a (top) bonding substrate on the second self-adhesive 30.

Figure 4:
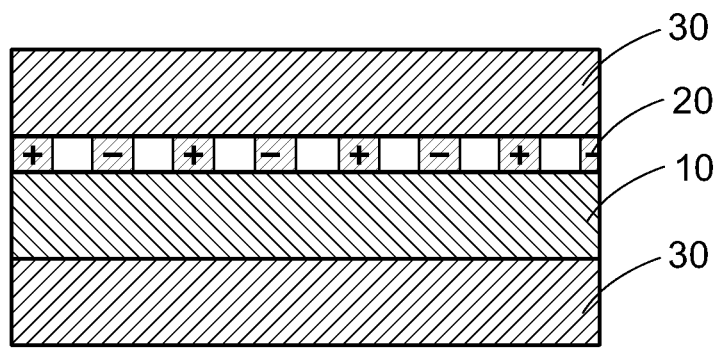
FIG. 4 shows a schematic representation of a longitudinal section through an inventive planar element having a perforate contacting element with dual comb structure and a third self-adhesive.

The inventive planar element depicted in FIG. 4 is identical to the planar element depicted in FIG. 2 with regard to the design and arrangement of the first self-adhesive 10, the contacting element 20 and the second self-adhesive 30. In contrast to the planar element depicted in FIG. 2, however, the planar element depicted in FIG. 4 has, on the bottom side of the first self-adhesive 10, a third self-adhesive 30, which allows better bonding of the planar element to a bonding substrate. Since in the present case the contacting element 20 contains both contacting electrodes of the first self-adhesive, the third self-adhesive can be selected arbitrarily, for instance—as in the example shown in FIG. 4—identically to the second self-adhesive 30. Instead of this, however, it would also be possible to use a pressure-sensitive adhesive, bringing advantages in the application of the planar element, since the element would not have to be heated during application. In the case of the use of a hotmelt adhesive as the first self-adhesive, a third self-adhesive may be realized, for example, in a simple way by virtue of the third self-adhesive being identical to the first self-adhesive, but a possible difference being that the third self-adhesive contains no conductive filler material, so that it would be possible with this adhesive to obtain a higher bond strength to the bonding substrate. If, in contrast, only one of the two contacting electrodes of the first self-adhesive were realized in the contacting element 20, then the third adhesive would have to be formed additionally as a self-adhesive which is a very good conductor of electrical current, in order that electrical contact could be ensured with an external counterelectrode.

Figure 5:
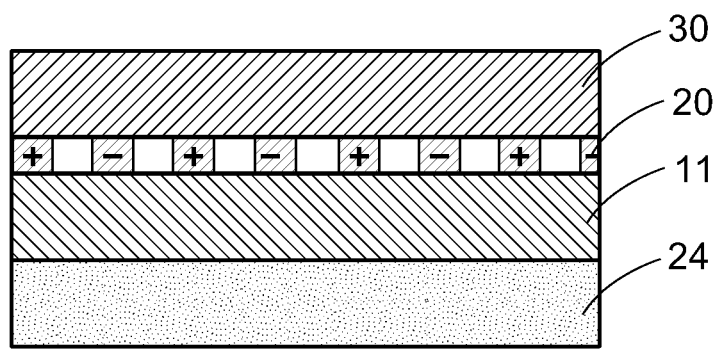
FIG. 5 shows a schematic representation of a longitudinal section through an inventive planar element which is lined with a temporary backing.

The inventive planar element depicted in FIG. 5 is identical to the planar element depicted in FIG. 2 in terms of the design and arrangement of the contacting element 20 and of the second self-adhesive 30; a difference lies in the first self-adhesive, which is formed as an intrinsically heatable posistor PSA 11. To protect the PSA 11 against unintended bonding even on chance contact, the PSA 11 is at least partly lined on the outside of the planar element, at the bottom, with a temporary backing 24.

The invention is described below by a number of exemplarily selected experiments, without wishing to suffer any restriction unnecessarily through the choice of the samples investigated.

The test methods set out below were used to characterize the inventive planar elements:

The bond strength of intrinsically heatable pressure-sensitive adhesives (PSAs) (test A) was determined in a peel test on a steel plate at an angle of 180° with a peel speed of 300 mm/min in accordance with ASTM D 3330-04. All of the measurements were conducted at room temperature (23° C.) under standardized conditions (at 50% relative humidity).

The bond strength of intrinsically heatable hotmelt adhesives (hotmelts) (test B) was determined in a T-peel force test. For this test a 200 µm thick strip of the hotmelt under investigation was sealed under reduced pressure to an untreated polyester film (Mitsubishi H) using a heating press at a temperature of 140° C. A strip 20 mm wide was cut from the resulting composite system and was conditioned under standard conditions for 24 h. Subsequently the heating film was peeled from the polyester backing again at room temperature, under standardized conditions, and the force required to achieve this was measured. Neither the hotmelt nor the polyester film was supported or fixed, and so a T-shaped peeling occurred. The results are reported in N/cm and are averaged from three measurements.

The determination of the electrical heatability (test C) for a planar element took place by measuring the increase in temperature following application of an electrical voltage. The temperature was measured using a Pt100 temperature sensor. The inventive planar element and the comparative example were applied with the adhesive side to a glass plate. A direct voltage of 12.8 volts was applied to the flexible heating element using a transformer. The temperature was measured directly on the surface of the glass plate after a time of 600 s. The results are reported in ° C.

In the course of the same test, the extent of the PTC effect was determined in respect of the same test specimens; for this purpose the time profile of the temperature which was established after subjection to current was recorded. The temperature in this case was measured as described above. Furthermore, the time profiles of current and voltage were recorded, allowing calculation in accordance with Ohm's law of the change in resistance.

Figure 9A:
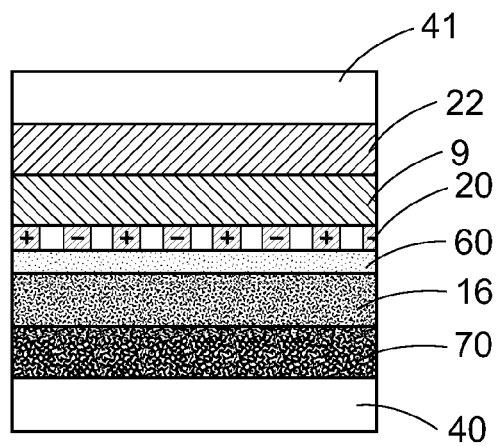
FIG. 9 shows a schematic representation of a longitudinal section through test constructions for determining the flexibility (low-temperature impact strength) and gap dimension bridging.
Figure 9B:
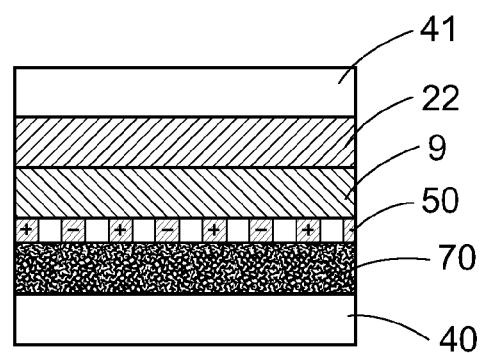

The flexibility of the planar element (test D) was determined by measuring the bowing of a strip of a planar element, the strip being 2 cm wide, 10 cm long and clamped in at one end, in the horizontal position under its own weight. This was done using the arrangement depicted schematically in FIG. 9. FIG. 9 depicts an assembly composed of an intrinsically heatable planar element, a top bonding substrate (glass sheet 41) and a bottom bonding substrate (substrate 40), the glass sheet 41 being connected to the intrinsically heatable hotmelt adhesive 9 on the top face of the planar element via a pressure-sensitive adhesive 22, and the substrate 40 being connected to the bottom face of the planar element via a double-sided adhesive tape 70. In the construction depicted in FIG. 9 *a*), the planar element is composed of the intrinsically heatable hotmelt adhesive 9 and an electrode structure 20, which is fastened to a backing material 16 by means of a laminating adhesive 60. In contrast, the inventive planar element depicted in FIG. 9 *b*) is composed of the intrinsically heatable hotmelt adhesive 9 and an electrically conductive ink 50 which is applied directly to said adhesive 9, and thus has no backing. In the construction used for test D, the glass plate 41 and the substrate 40 were omitted. The test was carried out without liner materials on the PSA surfaces. For this purpose the strip was cut out in such a way that the conductor tracks were essentially transverse to the longitudinal direction of the strip. All of the measurements were carried out at room temperature under standardized conditions.

The low-temperature impact strength of an assembly made up of a glass sheet and a support plate through the inventive planar element (falling ball test; test E) was used as a further indicator of the flexibility and as a qualitative measure of an anti-splintering effect. For this purpose the arrangements depicted in FIG. 9 were likewise used. For the test, samples with an area of 175×45 mm$^2$ were produced. The thickness of the glass sheet used was 2 mm. An acrylonitrile-butadiene-styrene (ABS) plastic was used as the bottom bonding substrate 40. Before measurement, the samples were kept in a freezer at −10° C. and not weighed until shortly before the test. A steel ball weighing 500 g was dropped onto the sample from a height of 1 m above it. After the impact of the steel ball on the glass plate, the sample was turned over, in order to remove all of the glass splinters detached as a result of impact. The remaining adhesive assembly was weighed again.

To determine the capacity to bridge differing gap dimensions (test F), the bonding strength between two bonding substrates having rough surfaces was employed. This was done using the arrangements depicted in FIG. 9, the glass plate 41 and the bottom substrate 40 being replaced by polyethylene plates having a roughness depth $r_z$ of 300 µm. In each case a circular diecut of a planar element having a diameter of 10 mm was pressed between the polyethylene plates with a force of 5 N for 10 s, it being ensured that exactly one conductor track ran through the diecut. After pressing, a measurement was made of the peel force perpendicular to the surface of the polyethylene plates (endface peel force). All of the measurements were conducted at room temperature under standardized conditions (23° C., 50% relative humidity).

As examples of inventive planar elements, planar elements were produced with a pressure-sensitive adhesive or a hotmelt adhesive as the first self-adhesive.

For the intrinsically heatable PSA, first of all a base PSA was prepared as disclosed in EP 04 712 016, possessing a comonomer composition of 44.5% by weight 2-ethylhexyl acrylate, 44.5% by weight n-butyl acrylate, 8% by weight methyl acrylate and 3% by weight acrylic acid. Determination of the molecular weight gave an average molecular weight $M_w$ of 650 000 g/mol with a polydispersity, $M_w/M_n$, of 7.0. The resulting base PSA was blended in solution with 40% by weight graphite (Timcal Timrex KS 6) and then applied by means of a coating bar to a siliconized glassine release paper (from Laufenberg). After 10 minute's drying at 120° C., the thickness of the resulting PSA layer was 100 µm.

Subsequently this PSA was crosslinked by means of electron beams. Electron bombardment took place using an instrument from Electron Crosslinking AB, Halmstad, Sweden. The coated PSA tape was guided via a chillroll, which is present as standard, beneath the Lenard window of the accelerator. In the zone of irradiation, the atmospheric oxygen was displaced by flushing with pure nitrogen. The belt speed was 10 m/min. The electron beam dose here was 50 kGy for an acceleration voltage of 180 kV for Example 1.

For the intrinsically heatable hotmelt, the base hotmelt used was an ethylene-vinyl acetate (EVA) copolymer of the Escorene Ultra FL 00728 (ExxonMobil) type with a vinyl acetate content of 28% by weight. Compounded into this base hotmelt, using a Haake Rheomix recording extruder at a temperature of 140° C. and a rotational speed of 120 $min^{-1}$, was 14% by weight of conductive carbon black (Printex XE2; Degussa) over a period of 45 minutes. The polymer compound obtained in this way was used via a vacuum press to produce a planar element having a thickness of 200 µm.

For Example 1, the construction depicted in FIG. 2 was employed, using the above-described intrinsically heatable PSA with a thickness of 100 µm as the first self-adhesive, the above-described base PSA with a thickness of 75 µm as the second self-adhesive, and a two-part contacting element, which was cut in the form of a comb from copper foil 0.03 mm thick and had a spacing of 1.5 mm. The size of the heatable area was 180 $cm^2$.

For Example 2, the construction depicted in FIG. 2 was employed, using the above-described intrinsically heatable hotmelt with a thickness of 150 µm as the first self-adhesive, the above-described base PSA with a thickness of 75 µm as the second self-adhesive, and a two-part contacting element, which was cut in the form of a comb from copper foil 0.03 mm thick and had a spacing of 1.5 mm. The conductor tracks of the contacting element were sealed onto the hotmelt at a temperature of 140° C. The size of the heatable area was 180 $cm^2$.

For Example 3, the construction depicted in FIG. 9 *b*) (without substrate 40 and glass plate 41) with the above-described intrinsically heatable hotmelt 9 in a thickness of 150 µm and also with the above-described base PSA 22 in a thickness of 75 µm was produced. The conductor tracks were produced using a conductive silver varnish which was applied directly to the heatable hotmelt. In terms of its adhesive bonding and heating functionality, this construction is directly comparable with the comparative examples.

For Comparative Example 1, a commercially available PTC heating element in accordance with the prior art, from an exterior mirror from Porsche, was used.

For Comparative Example 2, the construction depicted in FIG. 9 *a*) (without substrate 40 and glass plate 41) with the above-described intrinsically heatable hotmelt 9 in a thickness of 150 µm and also with the above-described base PSA 22 in a thickness of 75 µm was produced. This construction differs from Example 3 solely in the use of a flexible circuit board comprising copper tracks 30 µm thick on a polyester film 75 µm thick to contact the heatable hotmelt, and so comparing the properties of these two specimens is able to show directly the advantages of a backing-free form of the planar element, as a particular embodiment of the invention, relative to a form of the planar element having a permanent backing.

The bond strength was determined for the above-described base PSA and also for the above-described heatable PSA in accordance with test A:

| Base PSA: | 7.4 N/cm |
|---|---|
| Heatable PSA: | 6.3 N/cm |

The results of this test show that admixing a conductive filler to the base PSA leaves its pressure-sensitive adhesive properties largely the same.

The peel force was determined for the above-described base hotmelt and also for the above-described heatable hotmelt in accordance with test B:

| Base hotmelt: | 4.5 N/cm |
|---|---|
| Heatable hotmelt: | 3.1 N/cm |

The results of this test show that the admixing of a conductive filler to the base hotmelt leaves its hotmelt-adhesive properties largely the same.

The heatability and the PTC effect were determined for Example 1 and Example 2 and also for Comparative Example 1 in accordance with test C. In this test the planar elements attained the following temperatures:

| Example 1: | 53° C. |
|---|---|
| Example 2: | 64° C. |
| Comparative Example 1: | 54° C. |

The results of this test show that the inventive planar elements achieve a heating performance which corresponds to the heating performance of prior-art car mirror heating systems presently available on the market.

Figure 6:
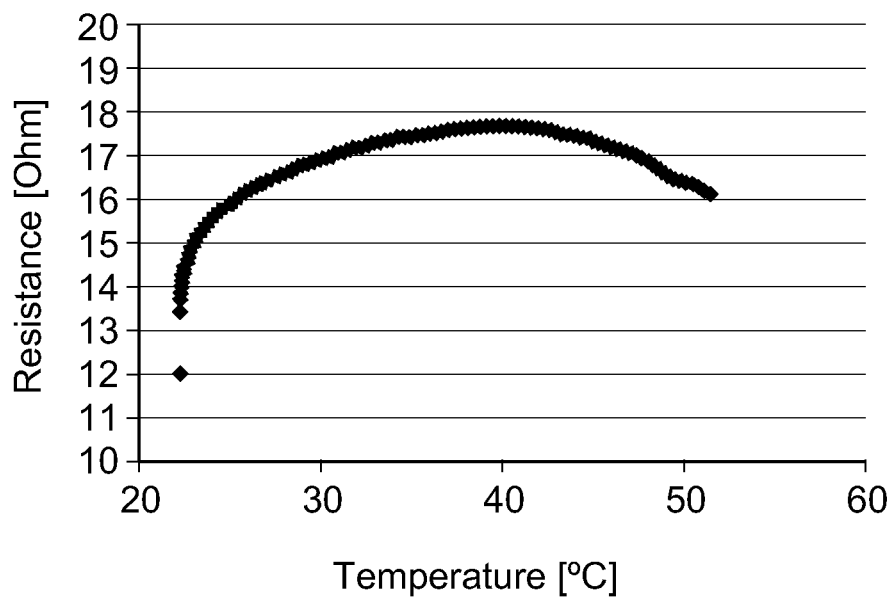
FIG. 6 shows a data curve in which the ohmic resistance of an inventive planar element (Example 1), determined for different temperatures, is depicted graphically.
Figure 7:
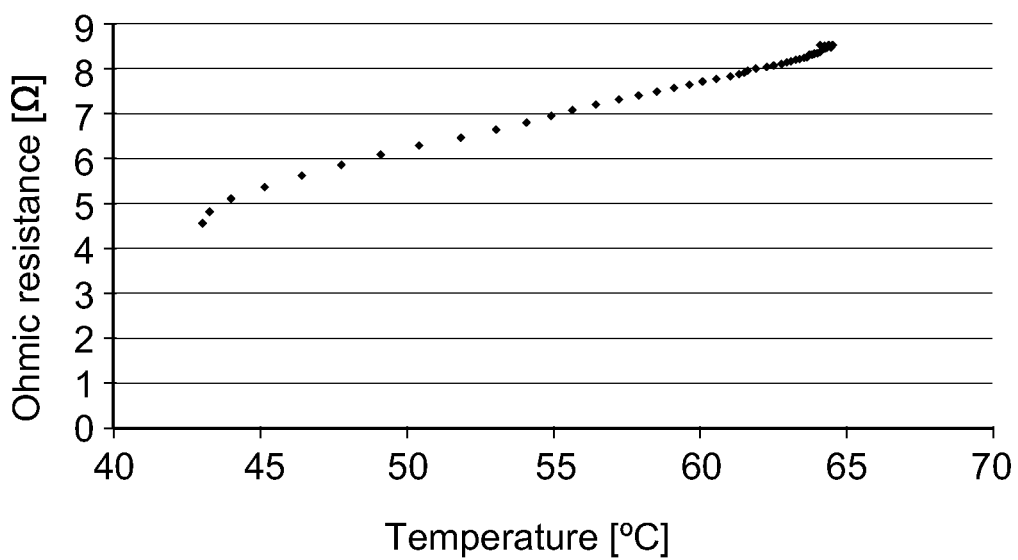
FIG. 7 shows a data curve in which the ohmic resistance of a further inventive planar element (Example 2), determined for different temperatures, is depicted graphically.
Figure 8:
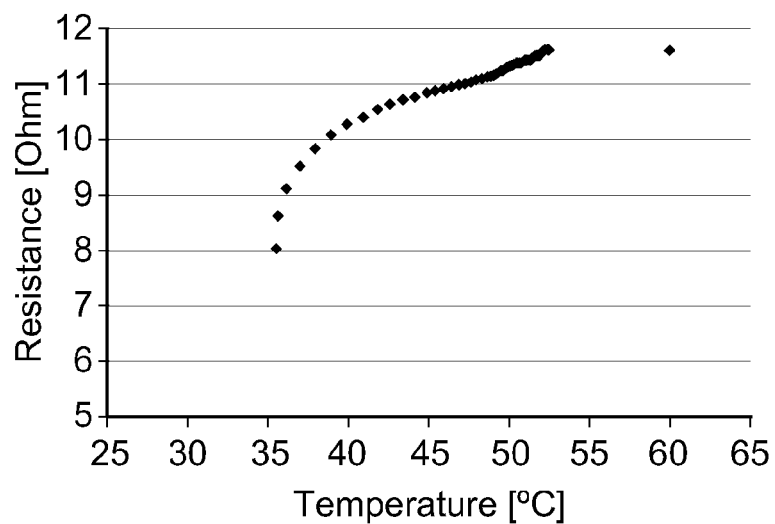
FIG. 8 shows a data curve in which the ohmic resistance of a commercial planar element as a reference example (Comparative Example 1), determined for different temperatures, is depicted graphically.

The overall resistance of the planar element, calculated from the instantaneous current and the respective instantaneous voltage, is shown as a function of temperature in FIG. 6, FIG. 7 and FIG. 8. The curve form obtained from these calculations offers indications of the PTC effect of the heating layers. FIG. 6 shows the results for Example 1, FIG. 7 the results for Example 2 and FIG. 8 the results for Comparative Example 1. Comparing the data curves obtained in these examples, it is apparent that the PTC effect is in some cases in fact more pronounced for the inventive planar elements than for the commercial comparative example.

The flexibility of the planar elements was determined for Example 3 (with the above-described heatable hotmelt) and also for the two Comparative Examples 1 and 2 in accordance with test D. The following bowings were measured:

| Example 3: | 70 mm |
|---|---|
| Comparative Example 1: | 15 mm |
| Comparative Example 2: | 35 mm |

The results of this test show that the inventive planar elements exhibit a considerably higher flexibility than the planar elements known from the prior art.

The flexibility and the anti-splintering protection of the planar elements were determined in accordance with test E for samples constructed in accordance with Example 3

(conductor tracks of conductive silver varnish, which is applied directly to the heatable hotmelt) and also for samples constructed in accordance with Comparative Example 2 (flexible circuit board with copper tracks 30 μm thick on a polyester film 75 μm thick). The samples possessed the constructions depicted in FIG. 9. In this case the conductor tracks applied from conductive silver varnish in Example 3 had the same geometry as the conductor structure on the flexible circuit board from Comparative Example 2. As a double-sided adhesive tape 70, tesa 4880 was used.

Figure 10:
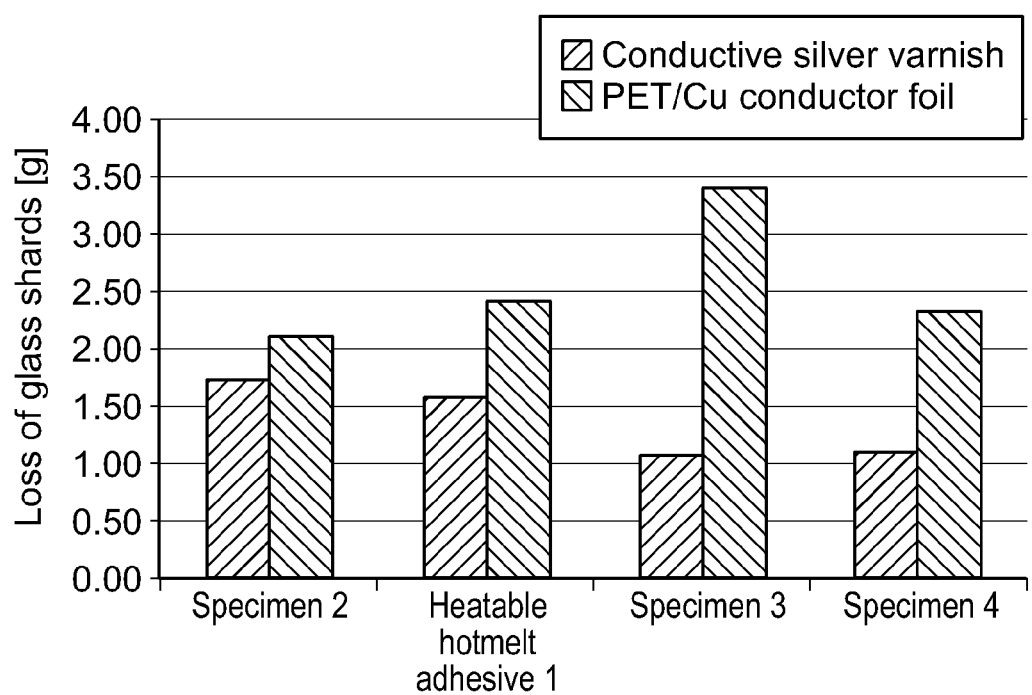
FIG. 10 shows a bar chart with data from the investigations for determining the low-temperature impact strength, for different planar elements.

FIG. 10 depicts the results of this test for four different sample systems, the results for each system being shown not only for the samples constructed in accordance with Example 3 ("conductive silver varnish") but also for the samples constructed in accordance with Comparative Example 2 ("PET/Cu conductor foil"). The sample systems differ in respect of the hotmelt-adhesive polymers used in each case and the conductive carbon black added (the results obtained for the above-described intrinsically heatable hotmelt are labelled with "heatable hotmelt adhesive 1").

The results of this test show that the loss of glass splinters for the particular variant of the inventive planar element as a backing-free planar element is consistently lower than in the case of the construction having a flexible circuit board with copper tracks 30 μm thick on a polyester film 75 μm thick. This demonstrates the fact that the inventive, backing-free construction in fact dissipates the energy transmitted on impact of the ball much more effectively and so leads to lower levels of glass fracture.

The capacity to bridge differing gap dimensions was determined as the bonding strength between two rough substrates in accordance with test F for the above-described intrinsically heatable hotmelt (Example 3) and also for Comparative Example 2. The maximum peel force determined in this test was as follows:

| Example 3: | 12.5 N |
|---|---|
| Comparative Example 2: | 8.5 N |

Likewise determined in this operation was the detachment energy as the integral of the detachment force over the detachment path:

| Example 3: | 2.8 Nmm |
|---|---|
| Comparative Example 2: | 1.7 Nmm |

The results of these tests show that, as a result of their greater flexibility, the inventive planar elements are significantly more capable of bridging a gap which comes about between two rough surfaces.

The exemplary experiments described above demonstrate the outstanding suitability of the flexible planar elements of the invention for obtaining a stable, heatable adhesive bond.

The invention claimed is:

1. A planar element having a first self-adhesive side face and a second adhesive side face, the planar element featuring a layer sequence comprising a heating layer, a contacting layer, and an adhesive layer;
   wherein the planar element is backing-free and flexible;
   wherein the heating layer is in contact, and in electrically conducting communication, with a first side face of the contacting layer;
   wherein the adhesive layer is in contact with a second side face of the contacting layer;
   wherein the heating layer is composed of an intrinsically heatable first self-adhesive designed as a posistor which heats up when an electric current is passed through;
   wherein the heating layer has a thickness of 20-200 μm;
   wherein the adhesive layer is composed of a second self-adhesive;
   wherein the contacting layer is an at least substantially two-dimensionally extended perforate contacting element;
   wherein the contacting layer is the only contacting layer in the planar element;
   wherein the contacting layer has a thickness of less than 20 μm;
   wherein the contacting layer consists of a conductive varnish, conductive ink, or conductive printing ink.

2. The planar element according to claim 1, wherein the perforate contacting element has reliefs whose principal extent runs at least substantially in one spatial direction.

3. The planar element according to claim 1, wherein the perforate contacting element has a branched comb structure or finger structure.

4. The planar element according to claim 1, wherein all sub-regions of the perforate contacting element are in electrically conducting connection with one another.

5. The planar element according to claim 1, wherein the perforation contacting element has at least two sub-regions which are not in electrically conducting connection with one another via the perforate contacting element.

6. The planar element according to claim 1, wherein the first self-adhesive comprises at least one electrically conductive filler.

7. The planar element according to claim 6, wherein the electrically conductive filler is selected from the group consisting of graphite, carbon nanoparticles, and carbon black.

8. The planar element according to claim 6, wherein the first self-adhesive features partially crystalline polymers.

9. The planar element according to claim 1, wherein the first self-adhesive and/or the second self-adhesive is a pressure-sensitive adhesive.

10. The planar element according to claim 1, wherein the first self-adhesive and the second self-adhesive are pressure-sensitive adhesives that undergo a permanent adhesive bond at room temperature with a substrate to which the planar element is adhered.

11. The planar element according to claim 1, wherein the first self-adhesive and/or the second self-adhesive is a hot melt adhesive.

12. The planar element according to claim 1, wherein the composition of first self-adhesive is identical to the composition of the second self-adhesive.

13. The planar element according to claim 1, wherein the composition of first self-adhesive is different to the composition of the second self-adhesive.

14. The planar element according to claim 1, wherein the planar element has a third self-adhesive on the side face of the heating layer that faces away from the perforate contacting element.

15. The planar element according to claim 1, which consists of four layers in the following sequence:
   heating layer-contacting layer-adhesive layer.

16. The planar element according to claim 1, which consists of four layers in the following sequence:
   additional adhesive layer-heating layer-contacting layer-adhesive layer;

wherein the additional adhesive layer is composed of a third self-adhesive that may be the same as or different from the second self-adhesive of the adhesive layer.

17. An adhesively bonded assembly comprising a bonding substrate adhered to a planar element according to claim 1.

18. An adhesively bonded assembly comprising a bonding substrate adhered to a planar element according to claim 15.

19. An adhesively bonded assembly comprising a bonding substrate adhered to a planar element according to claim 16.

20. A method of producing a planar element according to claim 1, comprising the steps of:
forming a first adhesive stratum,
applying the perforate contacting element directly to the surface of the first adhesive stratum, and
applying a second adhesive stratum to the surface of the perforate contacting element.

21. A method of heating an adhesively bonded assembly according to claim 17, said method comprising passing electric current through said planar element to cause said planar element to heat.

22. A method for adhesive bonding on the surface of a human or animal body, said method comprising adhering to the surface of the human or animal body a planar element according to claim 1, wherein the planar element comprises at least one active substance which can be released by heat or whose release is supported by heat.

23. A flexible planar element in backing-free form, the planar element consisting of either three or four layers, the three layers having the layer structure A, and the four layers having the layer structure B, wherein layer structure A has the layer sequence: heating layer-contacting layer-adhesive layer, and layer structure B has the layer sequence: additional adhesive layer-heating layer-contacting layer-adhesive layer, wherein the heating layer is in electrically conducting communication with the contacting layer, wherein the heating layer is composed of an intrinsically heatable first self-adhesive designed as a posistor that heats up when an electric current passes through it, wherein the heating layer has a thickness of 20-200 μm, wherein the contacting layer is an at least substantially two-dimensionally extended perforate contacting element, wherein the contacting layer is the only contacting layer in the planar element, wherein the contacting layer has a thickness of less than 20 μm, wherein the contacting layer consists of a conductive varnish, conductive ink, or conductive printing ink, wherein the adhesive layer is composed of a second self-adhesive, and wherein the additional adhesive layer is composed of a third self-adhesive that may be identical to or different from the second self-adhesive.

* * * * *